US011034754B2

(12) United States Patent
Falkenstein et al.

(10) Patent No.: US 11,034,754 B2
(45) Date of Patent: *Jun. 15, 2021

(54) METHOD FOR THE PURIFICATION OF ANTIBODIES

(71) Applicant: HOFFMANN-LA ROCHE INC., Little Falls, NJ (US)

(72) Inventors: Roberto Falkenstein, Munich (DE); Burkard Kolb, Eglfing (DE); Maria Sebald, Lenggries (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 245 days.

This patent is subject to a terminal disclaimer.

(21) Appl. No.: 15/458,368

(22) Filed: Mar. 14, 2017

(65) Prior Publication Data
US 2017/0183394 A1    Jun. 29, 2017

Related U.S. Application Data

(63) Continuation of application No. 14/271,058, filed on May 6, 2014, now Pat. No. 9,631,007, which is a continuation of application No. 11/920,288, filed as application No. PCT/EP2006/004863 on May 23, 2006, now abandoned.

(30) Foreign Application Priority Data

May 25, 2005 (EP) ..................... 05011302

(51) Int. Cl.
| | | |
|---|---|---|
| C07K 16/00 | (2006.01) | |
| B01D 15/36 | (2006.01) | |
| B01D 15/42 | (2006.01) | |
| C07K 16/06 | (2006.01) | |
| C07K 16/28 | (2006.01) | |
| C07K 16/32 | (2006.01) | |
| C07K 1/18 | (2006.01) | |
| G01N 30/96 | (2006.01) | |

(52) U.S. Cl.
CPC ............ C07K 16/00 (2013.01); B01D 15/362 (2013.01); B01D 15/363 (2013.01); B01D 15/426 (2013.01); C07K 1/18 (2013.01); C07K 16/065 (2013.01); C07K 16/2866 (2013.01); C07K 16/32 (2013.01); G01N 30/96 (2013.01); C07K 2317/50 (2013.01)

(58) Field of Classification Search
CPC combination set(s) only.
See application file for complete search history.

(56) References Cited

U.S. PATENT DOCUMENTS

| | | | |
|---|---|---|---|
| 4,136,094 A | 1/1979 | Condie | |
| 4,302,384 A | 11/1981 | Funatsu et al. | |
| 5,118,796 A | 6/1992 | Prior et al. | |
| 5,164,487 A | 11/1992 | Kothe et al. | |
| 5,429,746 A | 7/1995 | Shadle et al. | |
| 5,610,284 A * | 3/1997 | Ejima ................ | C07K 14/5412 435/69.52 |
| 6,069,236 A | 5/2000 | Burnouf-Radosevich et al. | |
| 6,162,904 A | 12/2000 | Mamidi et al. | |
| 6,281,336 B1 | 8/2001 | Laursen et al. | |
| 6,339,142 B1 * | 1/2002 | Basey ..................... | C07K 1/18 530/387.3 |
| 6,441,144 B1 | 8/2002 | Mamidi et al. | |
| 7,323,553 B2 | 1/2008 | Fahrner et al. | |
| 9,631,007 B2 * | 4/2017 | Falkenstein .......... | B01D 15/362 |
| 2002/0064526 A1 | 5/2002 | Pollack | |
| 2003/0229212 A1 | 12/2003 | Fahrner et al. | |
| 2004/0106780 A1 | 6/2004 | Suomela et al. | |
| 2004/0116674 A1 | 6/2004 | Ansaldi et al. | |
| 2005/0276812 A1 * | 12/2005 | Ebens, Jr. ............ | C07D 498/18 424/178.1 |

FOREIGN PATENT DOCUMENTS

| | | |
|---|---|---|
| CA | 1128418 | 7/1982 |
| DE | 3001187 | 7/1980 |
| DE | 3430320 | 3/1985 |
| DE | 3640513 | 6/1988 |
| EP | 0085747 | 8/1983 |
| EP | 0440483 | 8/1991 |
| EP | 0530447 | 3/1993 |
| EP | 0268973 | 6/1998 |
| EP | 1084136 | 3/2001 |
| EP | 1493751 | 1/2005 |
| EP | 1500661 | 1/2005 |
| WO | WO 1989/005157 | 6/1989 |

(Continued)

OTHER PUBLICATIONS

Hunt et al. ("Capillary isoelectric focusing and sodium dodecyl sulfate-capillary gel electrophoresis of recombinant humanized monoclonal antibody HER2" J. Chromatography A, 744 (1996) 295-301 (Year: 1996).*

Amersham Biosciences data file, Protein A Sepharose Fast Flow, 2002, pp. 1-4.

Amersham Biosciences, Ion Exchange Chromatography & Chromatofocusing, Principles & Methods Version 11-0004-21:1-188 (2004).

Andrew et al., Purificatin of Immunoglobulin M and Immunoglobulin D., Current Protocal in Immunology, 1997, John Wiley and Sons, Inc., total 8 pages.

(Continued)

*Primary Examiner* — Daniel E Kolker
*Assistant Examiner* — James L Rogers

(57) ABSTRACT

A method for the purification of immunoglobulins by ion exchange chromatography is described. The chromatographic method uses a weak ion exchange resin and a single step elution process for the purification of an immunoglobulin. Additionally a method for the determination of the salt concentration for the single step elution of an immunoglobulin from an ion exchange resin is described.

13 Claims, 20 Drawing Sheets

(56) References Cited

FOREIGN PATENT DOCUMENTS

| WO | WO 1993/004173 A1 | 3/1993 |
|---|---|---|
| WO | WO 1995/018155 | 7/1995 |
| WO | WO 1995/022389 | 8/1995 |
| WO | WO 1999/018130 | 4/1999 |
| WO | WO 1999/033484 | 7/1999 |
| WO | WO 1999/057134 | 11/1999 |
| WO | WO 1999/062936 | 12/1999 |
| WO | WO 1999/064462 | 12/1999 |
| WO | WO 2000/071142 | 11/2000 |
| WO | WO 2001/072844 | 10/2001 |
| WO | WO 2003/102132 | 12/2003 |
| WO | WO 2004/024866 | 3/2004 |
| WO | WO 2004/076485 | 9/2004 |
| WO | WO 2006/125599 | 11/2006 |

OTHER PUBLICATIONS

Boehringer Ingelheim Pharma GmbH & Co. KG, Statement of Grounds of Opposition to European Patent Publication No. EP 1 888 636 B1, filed Jun. 15, 2012 (30 pages).
Boehringer Ingelheim Pharma GmbH & Co., Experimental Report BI Pharma. 1-23 (Jun. 15, 2012).
Cacia et al., 1996, "Isomerization of an aspartic acid residue in the complementarity-determining regions of a recombinant antibody to human IgE: identification and effect on binding affinity," Biochemistry 35(6): 1897-1903.
Carboxylic Acids (last viewed on Nov. 9, 2010).
CM Affi-Gel Blue Gel Instruction Manual:1-7 (Jun. 21, 2012).
D10: Decision of Opposition Division on parent patent, EP 1888636 B, Jul. 24, 2014.
D12: WHO Informal Consultation on International Nonproprietary Names (INN), Policy for Blosmular Products, INN Working Document 07.211, Steptember 2006.
D13: Position paper "Policy Position on Naminng of Biotechonology-Derived Therapeutic Proteins", prepared in Oct. 2006, following the Sep. 2006 WHO conference in Geneva referred to in D12.
Danielsson et al., "One-step purification of monoclonal IgG antibodies from mouse ascites. An evaluation of different adsorption techniques using high performance liquid chromatography," J. Immunol. Methods 115(1):79-88 (1988).
Diagrams submitted Oct. 8, 2015, by Strawman Limited in Opposition Proceedings, in the Matter of Opposition to European. Patent Publication No. EP 2 261 252 B1 (2 pages).
European Patent Office, Communication pursuant to Article 101(1) and Rule 81(2) to (3) EPC dated Jun. 6, 2014, in the Matter of Opposition to European Patent Publication No. EP 1 888 636 B1 (18 pages).
European Patent Office, Interlocutory Decision dated Dec. 9, 2015, in the Matter of Opposition to European Patent Publication No. EP 2 261 252 B1 (11 pages).
European Patent Office, Interlocutory Decision dated Jul. 24, 2014, in the Matter of Opposition to European Patent Publication No. EP 1 888 636 B1 (15 pages).
European Patent Office, Preliminary Opinion dated Nov. 14, 2014, in the Matter of Opposition to European Patent Publication No. EP 2 261 252 B1 (11 pages).
European Patent Office, Preliminary Opinion dated Sep. 23, 2013, in the Matter of Opposition to European Patent Publication No. EP 1 888 636 B1 (16 pages).
European Search Report dated Feb. 21, 2011 in corresponding European Patent Application No. 10175706.0.
Everitt et al., "The pharmacokinetics, antigenicity, and fusion-inhibition activity of RSHZ19, a humanized monoclonal antibody to respiratory syncytial virus, in healthy volunteers", J Infect Dis., 174(3):463-469 (1996).
Experimental Report, "Comparison of the purification method of U.S. Pat. No. 5,429,746 (D27) to the single step purification method according to claim 1 of the new Main Request," cited in the oppositions of the co-pending European Patent Publication No. EP 1888636 on Apr. 10, 2013, (17 pages).
Express-ion High Flow Rate Ion Exchange Media:1 (Jun. 18, 2012).
F. Hoffmann-La Roche AG, Grounds of Appeal, filed Dec. 2, 2014, in the Matter of Opposition to European Patent Publication No. EP 1 888 636 B1 (57 pages).
F. Hoffmann-La Roche AG, Observations on Replies of Opponents to Grounds of Appeal, filed Oct. 6, 2015, in the Matter of Opposition to European Patent Publication No. EP 1 888 636 B1 (21 pages).
F. Hoffmann-La Roche AG, Observations on Reply of Opponent to Grounds of Appeal, filed Apr. 17, 2015, in the Matter of Opposition to European Patent Publication No. EP 1 888 636 B1 (12 pages).
F. Hoffmann-La Roche AG, Response to Communication to Rule 79(1) EPC, filed Apr. 10, 2013, in the Matter of Opposition to European Patent Publication No. EP 1 888 636 B1 (37 pages).
F. Hoffmann-La Roche AG, Response to Communication to Rule 79(1) EPC, filed Mar. 14, 2014, in the Matter of Opposition to European Patent Publication No. EP 2 261 252 B1 (25 pages).
F. Hoffmann-La Roche AG, Response to Summons to Attend Oral Proceedings pursuant to Rule 115(1) EPC, filed Dec. 23, 2013, in the Matter of Opposition to European Patent Publication No. EP 1 888 636 B1 (13 pages).
F. Hoffmann-La Roche AG, Response to Summons to Attend Oral Proceedings pursuant to Rule 115(1) EPC, filed Aug. 7, 2015, in the Matter of Opposition to European Patent Publication No. EP 2 261 252 B1 (17 pages).
F. Hoffmann-La Roche AG, Submission and Experimental Report (Nov. 6, 2009).
Fahrner et al., "Industrial purification of pharmaceutical antibodies: development, operation, and validation of chromatography processes," Biotechnol. Genet. Eng. Rev. 18:301-327 (2001).
First Declaration of Dr. Roberto Falkenstein, filed Mar. 13, 2014, in the Matter of Opposition to European Patent Publication No. EP 2 261 252 B1 (62 pages).
Follman et al., "Factorial screening of antibody purification processes using three chromatography steps without protein A," J. Chromatogr. A 1024(1-2):79-85 (2004).
GE Healthcare Life Sciences, "CM Sepharose Fast Flow," http://www.gelifesciences.cotn/webapp/wcs/stores/servlet/catalog/de/GELifeSciences (1 page); downloaded Jun. 14, 2012.
GE Healthcare Life Sciences, Statement of Grounds of Opposition to European Patent Publication No. EP 1 888 636 B1, filed Jun. 18, 2012 (9 pages).
GE Healthcare Life Sciences:1 (Jun. 14, 2012).
Giardina, 2003, "Chapter 25: Strategies for the purification of recombinant proteins," in: Makrides (Ed.) Gene Transfer and Expression in Mammalian Cells, pp. 641-659.
Glaxo Group Limited, Statement of Grounds of Opposition to European Patent Publication No. EP 1 888 636 B1, filed Jun. 21, 2012 (18 pages).
Goldenberg, "Trastuzumab, a recombinant DNA-derived humanized monoclonal antibody, a novel agent for the treatment of metastatic breast cancer," Clin. Ther. 21(2):309-318 (1999).
Hamilton, R. G., The Human IgG Subclasses:1-2 (1987).
Harris and Angai, (eds.), "Protein Purification Methods—a practical approach," Oxford University Press (1989), cover pages and pp. 192-195; 210-215, (8 pages).
Heide et al., The Plasma Proteins III (2nd Edition):1-29 (1977).
Human IgG (last viewed on Aug. 5, 2015).
Ishihara et al., "Optimization of monoclonal antibody purification by ion-exchange chromatography. Application of simple methods with linear gradient elution experimental data," J. Chromatogr. A 1069(1):99-106 (2005).
Jiskoot et al., "Two-step purification of a murine monoclonal antibody intended for therapeutic application in man. Optimisation of purification conditions and scaling up," J. Immunol. Methods. 124(1):143-156 (1989).
Johnston et al., "Equine antibodies to human gamma-G-globulin. II. Isolation and antigenic analysis of gamma-2- and gamma-1-antibody fractions from equine antisera to human gamma-G-globulin," J. Immunol. 100(5):942-954 (1968).
Josic et al., 2001, "Analytical and preparative methods for purification of antibodies," Food Technol. Biotechnol. 39(3): 215-226.

(56) References Cited

OTHER PUBLICATIONS

Kierkegaard & Perry, "Purification of IgG Using Protein A- or Protein G-Agarose," 2013 (2 pages). Retrieved from the Internet. URL:https://www.kpl.com/docs/techdocs/PURIFIGG.PDF.
Kirkegaard & Perry Laboratories Inc., 2013, "Purification of IgG using protein A- or protein G-agarose," www.kpl.com/docs.techdocs/purifigg.pdg.
Lottspeich, F. and Zorbas, H., Spektrum Akademischer Verlag, (1998), pp. 202-204.
Martin Huenges, Statement of Grounds of Opposition to European Patent Publication No. EP 1 888 636 B1, filed Jun. 21, 2012 (26 pages).
Mhatre et al., "Purification of antibody Fab fragments by cation-exchange chromatography and pH gradient elution," J. Chromatogr. A 707(2):225-231 (1995).
MorphoSys AG, Statement of Grounds of Opposition to European Patent Publication No. EP 1 888 636 B1, filed Jun. 15, 2012 (23 pages).
Necina et al., "Capture of human monoclonal antibodies from cell culture supernatant by ion exchange media exhibiting high charge density," Biotechnol. Bioeng. 60(6):689-698 (1998).
Opponent's Reference 15307-01 (Notice of Opposition for EP1888636, Sep. 21, 2011).
Opponent's Reference 1981EP-OP (Notice of Opposition for EP1888636, Sep. 21, 2011).
Opponent's Reference 70031 (Notice of Opposition for EP1888636, Sep. 21, 2011).
Opponent's Reference E 00132 (Notice of Opposition for EP1888636, Sep. 21, 2011).
Opponent's Reference JKB/OPP10216 (Notice of Opposition for EP1888636, Sep. 21, 2011).
Opponent's Reference M16911EP (Notice of Opposition for EP1888636, Sep. 21, 2011).
Opponent's Reference MS180 (Notice of Opposition for EP1888636, Sep. 21, 2011).
Pall Life Sciences, "Q & CM HyperZ Ion Exchange Sorbents" Pall Life Sciences:1-8 (Dec. 1, 2004).
Pall Life Sciences, "Q, S, Deae, CM Ceramic HyperD" Pall Life Sciences:1-8 (Dec. 1, 2004).
Presta et al., 1993, "Humanization of an antibody directed 2623-2632 against IgE," J. Immunology 151(5): 2623-2632.
Protein Purification Methods (A Practical Approach), 1989, Eds. Harris and Angal, Oxford University Press, pp. 192-195 and 210-215.
Redwan et al., "Production and purification of ovine anti-tetanus antibody," Comp. Immunol. Microbiol. Infect Dis. 28(3):167-176 (2005) (Epub Feb. 16, 2005).
Roque et al., 2004 "Antibodies and genetically engineered related molecules: production and purification," Biotechnol. Prog. 20(3): 639-654.
Sabine Teschner, Statement of Grounds of Opposition to European Patent Publication No. EP 1 888 636 B1, filed Jun. 19, 2012 (19 pages).
Satinder Ahuja (ed.), Handbook of Bioseparations, Chapter 15 (2000), cover pages and pp. 535 and 563, (4 pages).
Satinder Ahuja (ed.), Handbook of Bioseparations, Chapter 15 (2000), "Separation of Antibodies by Liquid Chromatography," cover page and pp. 535-632 (99 pages).
Schwarz et al., LaborPraxis:62-66 (Jun. 1997).
Second Declaration of Dr. Roberto Falkenstein, filed Aug. 3, 2015, in the Matter of Opposition to European Patent Publication No. EP 2 261 252 B1 (14 pages).
Sigma Aldrich, Technical Information concerning sodium citrate buffer solutions:1-3, Retrieved from the Internet on Jun. 20, 2012. URL:http://www.sigmaaldrich.com/catalog/product/FLUKA/82587?lang—de®ion—DE.
Staby et al., "Comparison of chromatographic ion-exchange resins IV. Strong and weak cation-exchange resins and heparin resins," J. Chromatogr. A. 1069(1):65-77 (2005).
Strawman Limited, Grounds of Appeal, filed Apr. 15, 2016, in the Matter of Opposition to European Patent Publication No. EP 2 261 252 B1 (20 pages).
Strawman Limited, Rule 116 Submission, filed Aug. 4, 2015, in the Matter of Opposition to European Patent Publication No. EP 2 261 252 B1 (21 pages).
Strawman Limited, Statement of Grounds of Opposition to European Patent Publication No. EP 1 888 636 B1, filed Jun. 22, 2012 (26 pages).
Strawman Limited, Statement of Grounds of Opposition to European Patent Publication No. EP 2 261 252 B1, filed Apr. 24, 2013 (11 pages).
Stucki et al., "Characterisation of a chromatographically produced anti-D immunoglobulin product," J. Chromatogr. B Biomed. Sci. Appl. 700(1-2):241-248 (1997).
Tanaka et al., "High quality human immunoglobulin G purified from Cohn fractions by liquid chromatography," Braz. J. Med. Biol. Res. 33(1):27-30 (2000).
The Communication of a notice of opposition by the European Patent Office, issued on May 10, 2013, in the co-pending European Patent No. EP 226125, (19 pages).
The opposition statement in the related European Patent No. 2261252, which was notified by the European Patent Office on Aug. 10, 2015.
Tishchenko et al., "Effect of salt concentration gradient on separation of different types of specific immunoglobulins by ion-exchange chromatography on DEAE cellulose," J. Chromatogr. B Biomed. Sci. Appl. 706(1):157-166 (1998).
Tosoh Bioscience, Toyopearl Orientation Sheet, cited in the oppositions of the co-pending European Patent Publication No. EP 1888636 on Apr. 10, 2013, (1 page).
Whatman Ltd., "Express-Ion High Flow Rate Ion Exchange Media," 2007-2009, retrieved from the Internet. http://www.whatman.com/EXPRESSIONHighFlowRateIonExchangeMedia (1 page); downloaded Jun. 18, 2012.
Whatman Ltd., Cation Exchange Celluloses; 2007-2009, retrieved from the Internet. http://www.whatman.com/CationExchangeCelluloses.aspx (1 page).
Wheelwright, S.M., "Protein Purification: Design and Scale up of Downstream Processing," Hanser Publishers (1991), cover pages and pp. 142-145; 164-169; 216-217 (8 pages).
Yu et al., "Purification of antibodies from protein mixtures and mouse ascites fluid using Zeolite X," Biotechnol. Prog. 14(2):332-337 (1998).

\* cited by examiner

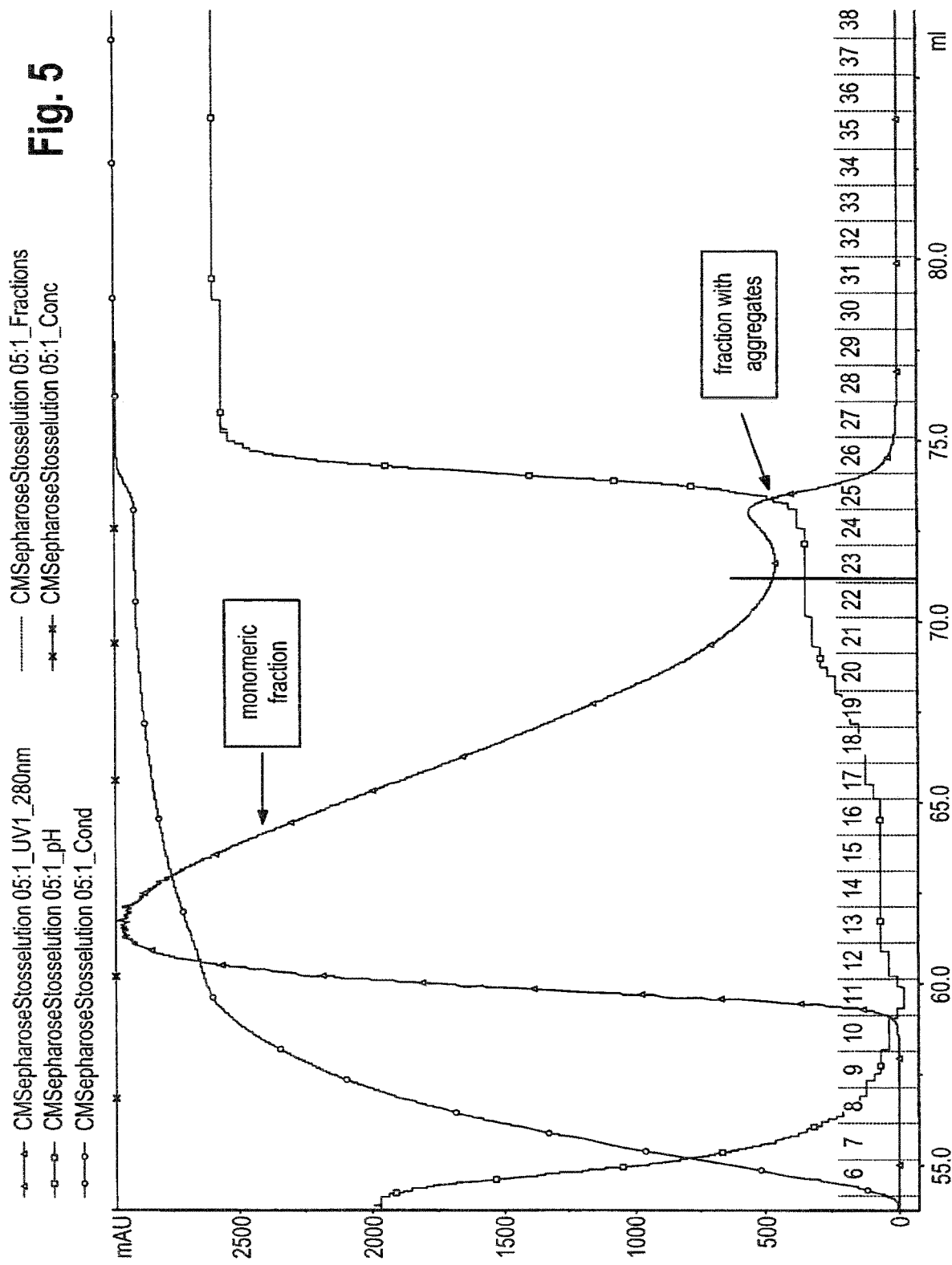

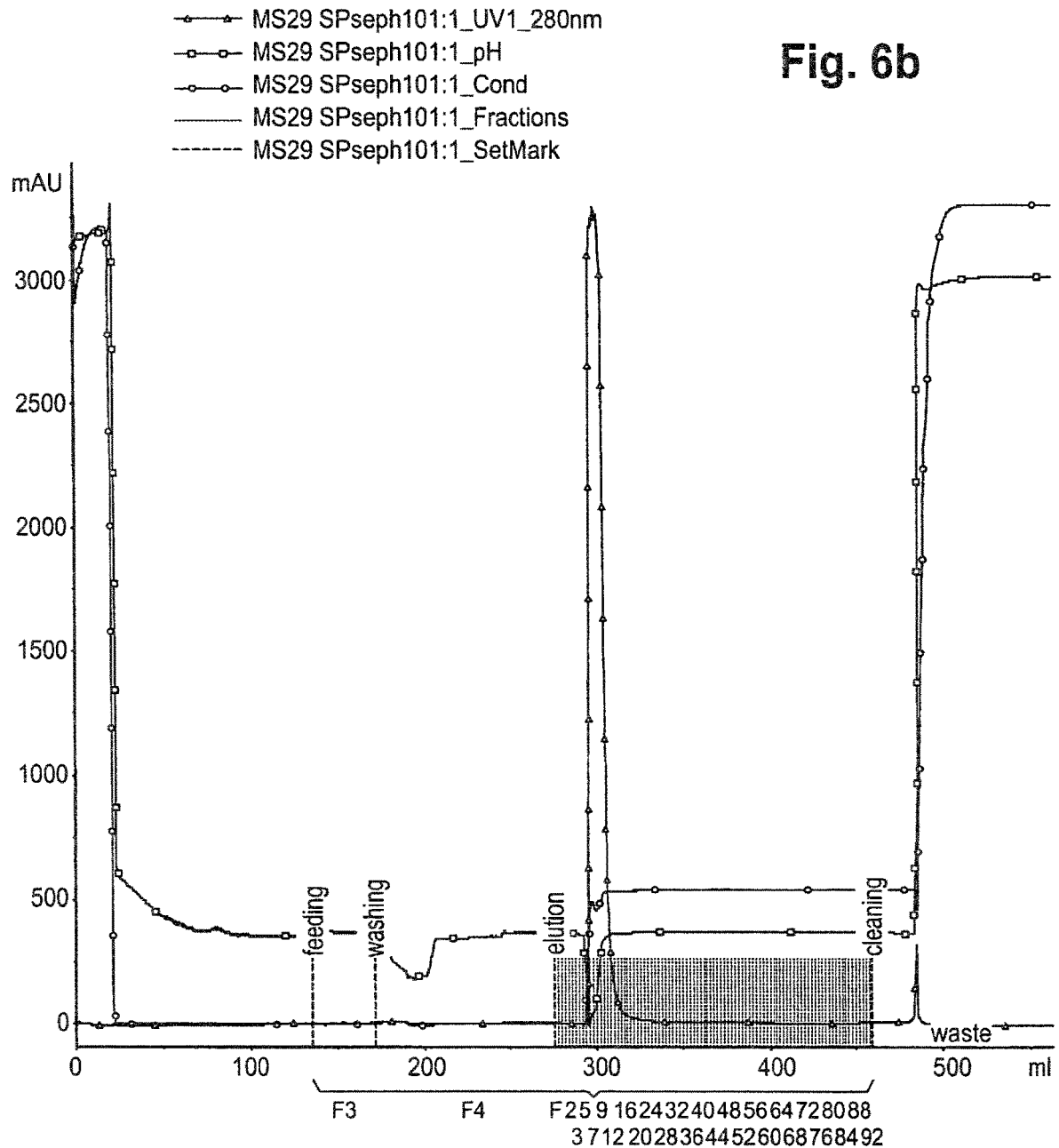

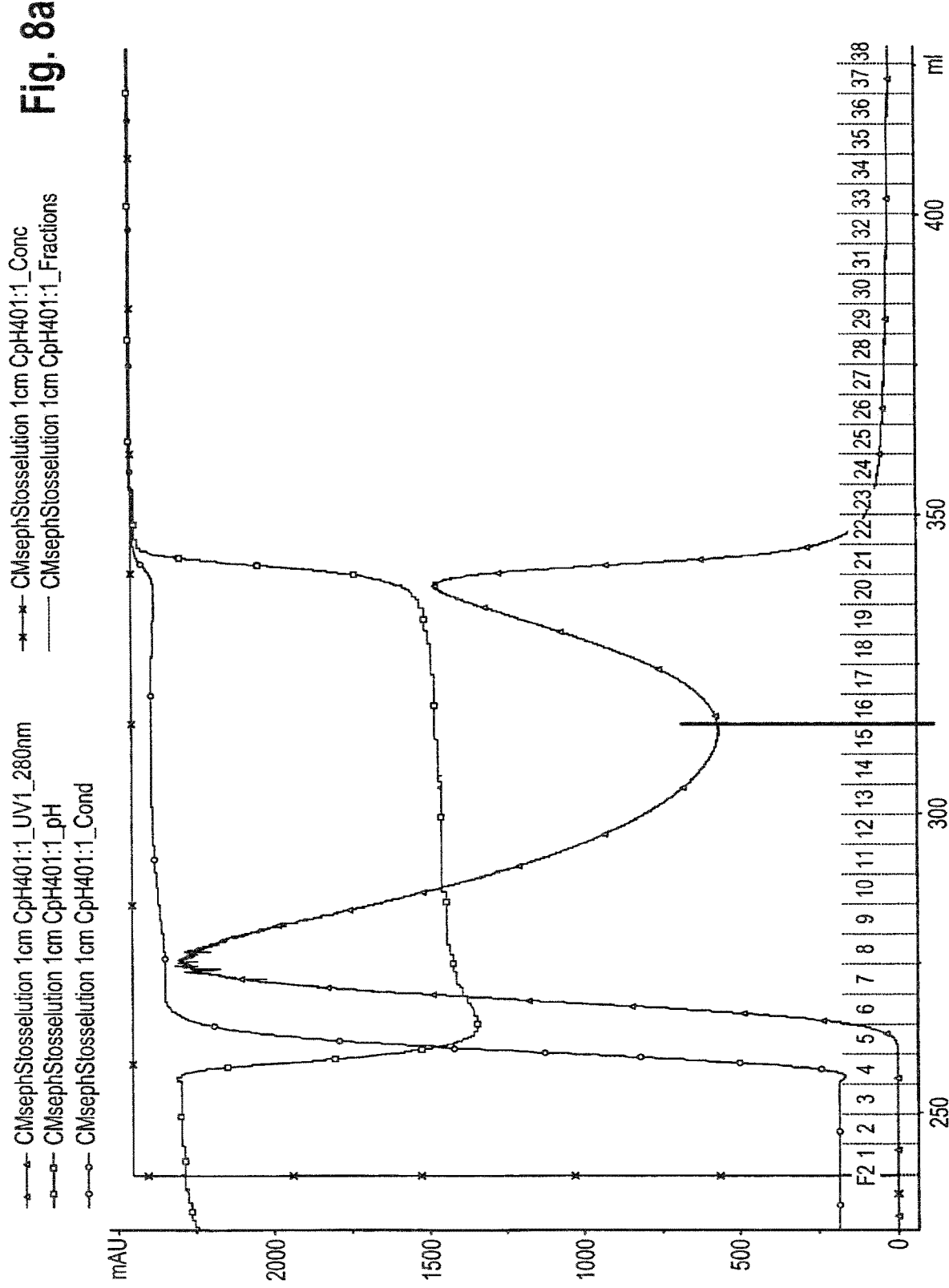

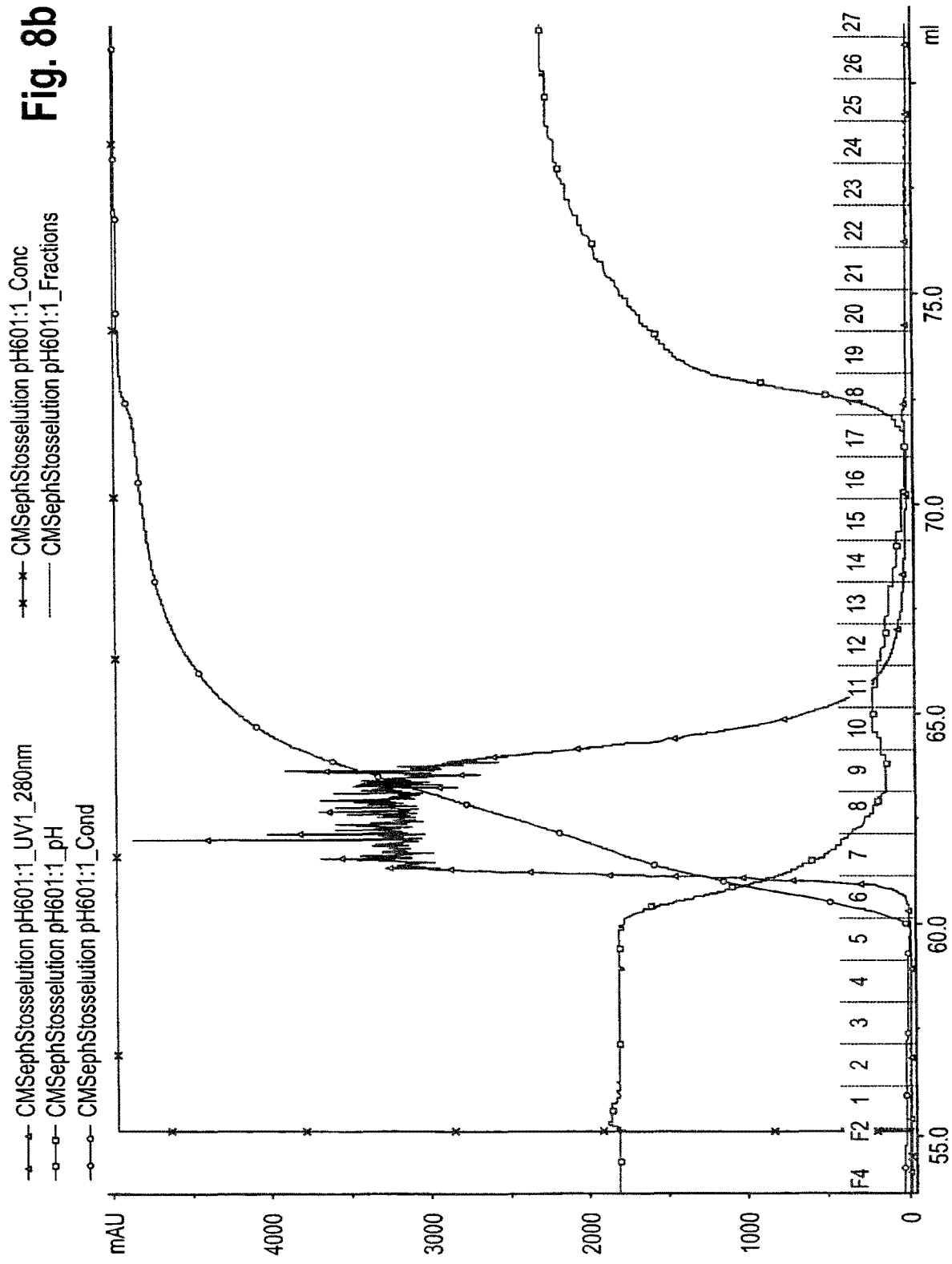

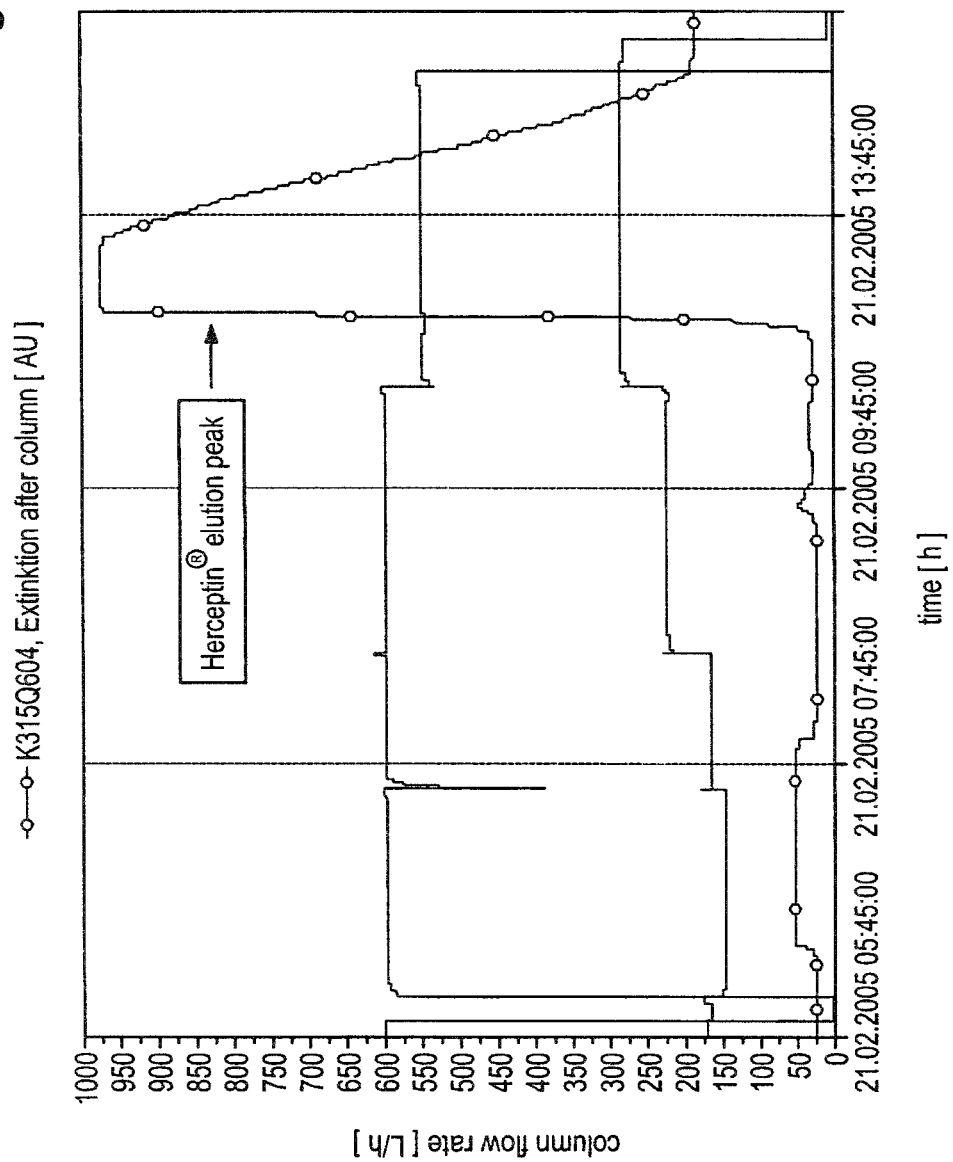

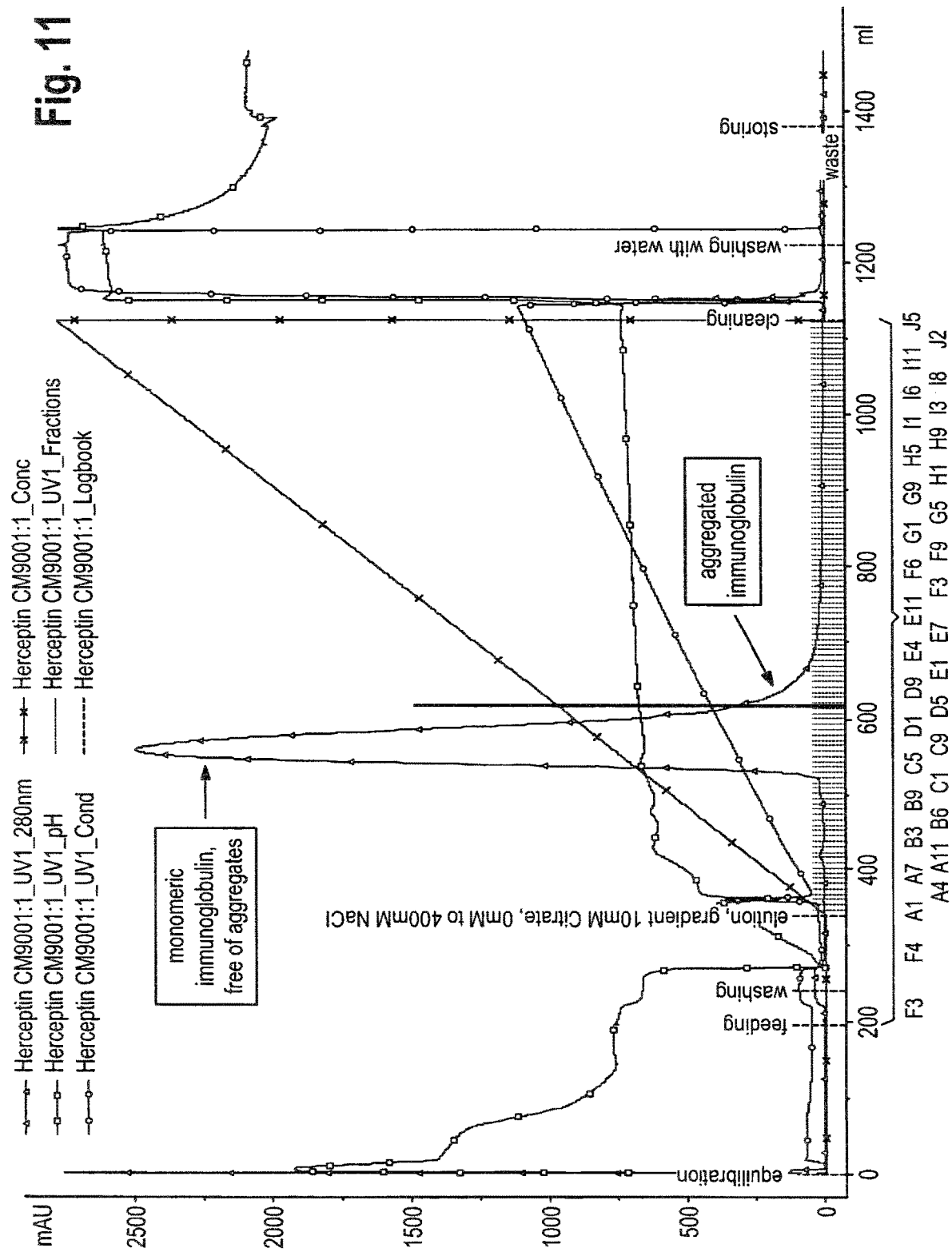

METHOD FOR THE PURIFICATION OF ANTIBODIES

CROSS REFERENCE TO RELATED APPLICATIONS

This application is a continuation of U.S. patent application Ser. No. 14/271,058, filed May 6, 2014, which is a continuation of U.S. patent application Ser. No. 11/920,288, filed Nov. 13, 2007, now abandoned, which is a U.S. National Stage Application under 35 U.S.C. § 371 of International Patent Application No. PCT/EP2006/004863, filed May 23, 2006, which claims the benefit of priority to European Patent Application No. 05011302.6, filed May 25, 2005, the content of each of which is incorporated by reference herein in its entirety.

FIELD OF THE INVENTION

The current invention relates to the field of polypeptide purification. A novel method for the purification of immunoglobulins with an ion exchange resin is described herein. At the same time a method for the fast determination of purification conditions is given.

BACKGROUND OF THE INVENTION

Proteins and especially immunoglobulins play an important role in today's medical portfolio. For human application every pharmaceutical substance has to meet distinct criteria. To ensure the safety of biopharmaceutical agents to humans nucleic acids, viruses, and host cell proteins, which would cause severe harm, have to be removed especially. To meet the regulatory specification one or more purification steps have to follow the manufacturing process. Among other, purity, throughput, and yield play an important role in determining an appropriate purification process.

Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

Necina, R. et al., Biotechnol. Bioeng. 60 (1998) 689-698, reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immun. Meth. 115 (1988), 79-88.

A combination of methods, i.e. a caprylic acid precipitation and ion exchange chromatography, was used by Raweerith, R. et al. (J. Immun. Meth. 282 (2003) 63-72), as means to fractionate pepsin-digested horse antivenom F(ab')$_2$ antibody. In WO 2003/102132 the combination of a non-affinity purification step and a high-performance tangential-flow filtration is reported for the purification of proteins. The combination of two affinity chromatography steps is reported in WO 92/19973.

Follman, D. K., and Fahrner, R. L., reported a factorial screening of antibody purification processes using three chromatography steps without protein A (J. Chrom. A 1024 (2004) 79-85). Mhatre, R. et al. (J. Chrom. A 707 (1995) 225-231), explored the purification of antibody Fab fragments by cation exchange chromatography and pH gradient elution.

WO 94/00561 reports human monoclonal anti-rhesus antibodies and cell lines producing the same. A method for purifying a polypeptide by ion exchange chromatography is reported in WO 2004/024866 in which a gradient wash is used to resolve a polypeptide of interest from one or more contaminants. Schwarz, A. et al. (Laborpraxis 21 (1997) 62-66), report the purification of monoclonal antibodies with a CM-HyperD-column.

WO 2004/076485 reports a process for antibody purification by protein A and ion exchange chromatography. In EP 0 530 447 a process for purifying IgG monoclonal antibodies by a combination of three chromatographic steps is reported. The removal of protein A from antibody preparations is reported in U.S. Pat. No. 4,983,722.

WO 95/16037 reports the purification of anti-EGF-R/anti-CD3 bispecific monoclonal antibodies from hybrid hybridoma performed by protein A cation exchange chromatography. The separation of antibody monomers from its multimers by use of ion exchange chromatography is reported in EP 1 084 136. U.S. Pat. No. 5,429,746 relates to the application of hydrophobic interaction chromatography combination chromatography to the purification of antibody molecule proteins.

SUMMARY OF THE INVENTION

Thus it is the objective of the current invention to provide another method for the purification of recombinantly produced immunoglobulins and for the separation of monomeric and multimeric immunoglobulin species.

The current invention provides a method for purifying an immunoglobulin, wherein the method comprises the following steps
  a) providing a solution comprising an immunoglobulin, a buffer substance, and optionally a salt;
  b) bringing the solution and a weak ion exchange material in contact under conditions whereby the immunoglobulin binds to the weak ion exchange material;
  c) recovering the immunoglobulin from the weak ion exchange material in a single step by using a solution comprising a buffer substance and a salt.

The invention further provides a method for determining the concentration of a salt for eluting a polypeptide from an ion exchange chromatography material in a single step purification process, comprising the following two steps
  a) step one comprising the following sub-steps
    a1) providing a solution comprising a polypeptide, a buffer substance, and optionally a salt;
    a2) bringing a first aliquot of the solution containing the polypeptide and an ion exchange material in contact under conditions whereby the polypeptide binds to the ion exchange material;
    a3) recovering the polypeptide from the ion exchange material by using a solution comprising a buffer substance and a salt whereby the concentration of the salt is increased linearly;

a4) determining the starting concentration of the salt where the first fraction of the polypeptide starts to elute from the ion exchange column;
b) step two comprising the following sub-steps
b1) bringing a second aliquot of the solution containing the polypeptide and an ion exchange material in contact under conditions whereby the polypeptide binds to the ion exchange material;
b2) recovering the polypeptide from the ion exchange material by using a three step elution method, whereby
i) the salt concentration of the first elution step is calculated as the sum of
the product of the starting concentration of the salt as determined in step a4) and the total number of monovalent cations different from hydrogen denoted in the molecular formula of the salt
and
the product of the concentration of the buffer salt and the total number of monovalent cations different from hydrogen denoted in the molecular formula of the buffer salt;
ii) the salt concentration of the second elution step is the product of the salt concentration of the first elution step and a factor between 1.25 and 1.35;
iii) the salt concentration of the third elution step is the product of the salt concentration of the first elution step and a factor between 1.50 and 1.70;
whereby the factors of step ii) and iii) are determined as follows: at a starting concentration between 10 mM and 40 mM the factors are 1.35 and 1.70 respectively, at a starting concentration between 40 mM and 70 mM the factors are 1.30 and 1.60 respectively, and at a starting concentration of more than 70 mM the factors are 1.25 and 1.50 respectively.
b3) determining at which sub-step of the three step elution method of step b2) the polypeptide is eluted from the ion exchange column thereby determining the concentration of a salt for eluting a polypeptide from an ion exchange chromatography material in a single step purification process.

DETAILED DESCRIPTION OF THE INVENTION

These terms are used within this application in accordance with the following definition:

The term "ion exchange resin" or "ion exchange material" as used within this application denotes an immobile high molecular weight matrix that carries covalently bound charged substituents. For overall charge neutrality not covalently bound counter ions are bound thereto. The "ion exchange material" has the ability to exchange its not covalently bound counter ions for similarly charged ions of the surrounding solution. Depending on the charge of its exchangeable counter ions the "ion exchange resin" is referred to as cation exchange resin or as anion exchange resin. Depending on the nature of the charged group (substituent) the "ion exchange resin" is referred to as, e.g. in the case of cation exchange resins, sulfonic acid resin (S), or carboxymethyl resin (CM). Depending on the chemical nature of the charged group/substituent the "ion exchange resin" can additionally be classified as strong or weak ion exchange resin, depending on the strength of the covalently bound charged substituent. For example, strong cation exchange resins have a sulfonic acid group as charged substituent, weak cation exchange resins have a carboxylic group, preferably a carboxymethyl group, as charged substituent, and weak anion exchange resins have a diethylaminoethyl group as charged substituent.

Cation exchange resins are available under different names from a multitude of companies such as e.g. Bio-Rex, Macro-Prep CM (available from Biorad Laboratories, Hercules, Calif., USA), weak cation exchanger WCX 2 (available from Ciphergen, Fremont, Calif., USA), Dowex® MAC-3 (available from Dow chemical company—liquid separations, Midland, Mich., USA), Mustang C (available from Pall Corporation, East Hills, N.Y., USA), Cellulose CM-23, CM-32, CM-52, hyper-D, and partisphere (available from Whatman plc, Brentford, UK), Amberlite® IRC 76, IRC 747, IRC 748, GT 73 (available from Tosoh Bioscience GmbH, Stuttgart, Germany), CM 1500, CM 3000 (available from BioChrom Labs, Terre Haute, Ind., USA), and CM-Sepharose™ Fast Flow (available from GE Healthcare—Amersham Biosciences Europe GmbH, Freiburg, Germany).

Preferably, the charged substituents of the weak ion exchange material are at least about 90% carboxylic acid groups, more than 90% carboxylic acid groups, or more than 95% carboxylic acid groups.

The terms "single step elution" and "single step gradient elution", which are used interchangeably within this application, denote a method wherein e.g. the concentration of a substance causing elution, i.e. the dissolution of a bound compound from a material, is raised or lowered at once, i.e. directly from a starting value/level to a final value/level, i.e. in a single step.

A "polypeptide" is a polymer of amino acid residues joined by peptide bonds, whether produced naturally or synthetically. Polypeptides of less than about 20 amino acid residues are referred to as "peptides."

A "protein" is a macromolecule comprising one or more polypeptide chains or a polypeptide chain of more than 100 amino acid residues. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "antibody" and "immunoglobulin" which can be used interchangeably within this application comprise at least two light polypeptide chains and two heavy polypeptide chains. Each of the heavy and light polypeptide chains contains a variable region (generally the amino terminal portion of the polypeptide chain) which contains a binding domain for interaction with the antigen. Each of the heavy and light polypeptide chains also comprises a constant region (generally the carboxyl terminal portion) which may mediate the binding of the antibody to host tissues or factors including various cells of the immune system, some phagocytic cells and a first component (C1q) of the classical complement system. Typically, the light and heavy polypeptide chains are complete chains, each consisting essentially of a variable region, i.e. $V_L$ or $V_H$, and a complete constant region, i.e. of $C_L$ in case of a light polypeptide chain or of $C_H1$, $C_H2$, $C_H3$, and optionally $C_H4$ in case of a heavy polypeptide chain. The variable regions of the antibody according to the invention can be grafted to constant regions of other isotypes. For example, a polynucleotide encoding the variable region of a heavy chain of the 1-isotype can be grafted to polynucleotide encoding the constant region of another heavy chain class (or subclass).

As used herein, the term "antibody" or "immunoglobulin" refers to a protein consisting of one or more polypeptides substantially encoded by antibody genes. The recognized antibody genes include the different constant region genes as well as the myriad antibody variable region genes. Antibodies may exist in a variety of forms, including, for example, Fv, Fab, and F(ab)2 as well as single chains (e.g. Huston, J. S., et al., PNAS USA 85 (1988) 5879-5883; Bird et al., Science 242 (1988) 423-426; and, in general, Hood et al., Immunology, Benjamin N.Y., 2nd edition (1984) and Hunkapiller and Hood, Nature 323 (1986) 15-16). In one embodiment antibodies according to the invention comprise monoclonal antibodies and fragments thereof, for example isolated heavy or light chains, or heavy or light chains only consisting of constant regions as well as fragments thereof.

General chromatographic methods and their use are known to a person skilled in the art. See for example, Chromatography, $5^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science By, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

The current invention provides a method for purifying an immunoglobulin, wherein the method comprises the following steps
 a) providing a solution comprising an immunoglobulin, a buffer substance, and optionally a salt;
 b) bringing the solution and a weak ion exchange material in contact under conditions whereby the immunoglobulin binds to the weak ion exchange material;
 c) recovering the immunoglobulin from the weak ion exchange material in a single step by using a solution comprising a buffer substance and a salt.

The purification process of immunoglobulins in general comprises a multistep chromatographic part. In the first step non-immunoglobulin polypeptides and proteins are separated from the immunoglobulin fraction by an affinity chromatography, e.g. with protein A. Afterwards an ion exchange chromatography can be performed to disunite the individual immunoglobulin classes and to remove traces of protein A, which has been coeluted from the first column. Finally a third chromatographic step is necessary to separate immunoglobulin monomers from multimers and fragments of the same class. Sometimes the amount of aggregates is high (5% or more) and it is not possible to separate them efficiently in the third purification step necessitating further purification steps.

With the recombinant production of specific immunoglobulins the separation step for the separation of different immunoglobulin classes is dispensable. Thus the overall purification process of recombinantly produced immunoglobulins may be reduced to two chromatographic steps.

The conditioned protein A eluate is in general chromatographically processed on a cation exchange material at pH values below the isoelectric point of the respective immunoglobulin protein.

The anti IL-1R antibody (WO 2005/023872) and Herceptin®, an anti-HER2 antibody (WO 99/57134), were available in sufficient quantities in our laboratories at the time of the invention and therefore the current invention is exemplified with these two immunoglobulins. Likewise the invention is in general practicable with immunoglobulins. This exemplified description is done only by way of example and not by way of limitation of the invention. These examples are provided to aid the understanding of the present invention, the true scope of which is set forth in the appended claims.

The current invention describes a purification method for the separation of immunoglobulin monomers from aggregates and fragments as well as the depletion of other polypeptide impurities. As can be seen from the experiments this purification is achieved by the use of weak ion exchange resins, preferably by the use of weak cation exchange resins. As exemplified by the comparison of strong and weak ion exchange materials the weak ion exchange material provides a separation of monomeric and aggregated forms of the immunoglobulins (see examples 1 and 2 and examples 9 and 12).

In one embodiment of the invention the pH value of the buffer material (substance) is of from pH 3.0 to pH 10.0, preferably of from pH 3.0 to pH 7.0, more preferred of from pH 4.0 to pH 6.0 and most preferred of from pH 4.5 to pH 5.5.

In one embodiment the pH value is kept constant in the single step, i.e. it is maintained at the same value in the single step.

Another preferred item of the current invention is that the method of the current invention is applicable to immunoglobulins that have an isoelectric point (pI) of 6.0 or more (pI≥6.0) and therefore have a net positive charge in the pH range starting from pH 6.0 to pH 14.

A preferred embodiment of the invention is the purification of an immunoglobulin of the IgG or IgE class.

A weak cation exchange material is used in a preferred embodiment of the current invention.

The buffer material is preferably employed in a concentration range between 5 mM and 100 mM as exemplified.

For the recovering of the bound immunoglobulins from the weak ion exchange material the conductivity of the buffer/solution is increased. This can be accomplished either by an increased buffer salt concentration or by the addition of other salts, so called elution salts, to the buffer solution. Preferred elution salts are sodium citrate, sodium chloride, sodium sulphate, sodium phosphate, potassium chloride, potassium sulfate, potassium phosphate, as well as other salts of citric and phosphoric acid, and any mixture of these components. Especially preferred are sodium citrate, sodium chloride, potassium chloride and mixtures thereof.

The concentration of the salt, causing the elution, is preferably in the range of between 5 mM and 500 mM, more preferred between 5 mM and 400 mM, and especially preferred between 5 mM and 250 mM.

Another preferred embodiment of the invention is the use of the salt, causing the elution, at the same time as buffer substance, especially with citric acid and salts thereof or phosphoric acid and salts thereof.

The method of the current invention is preferably a chromatographic or batch method, especially preferred is a method comprising a batch elution.

Another preferred embodiment of the current invention is that the purification is a single step purification process.

A "single step" denotes a process wherein one or more conditions, for example the pH, the ionic strength, concentration of a salt, and/or the flow of a chromatography, is/are changed all at once from a starting value to a final value, i.e. the conditions are changed incrementally, i.e. stepwise, in contrast to a linear change.

Still a preferred embodiment of the current invention is that the method comprises the additional step of a purification of the immunoglobulin by a protein A affinity chromatography before step a) of the method.

The current invention further provides a method for determining the concentration of a salt for eluting a polypeptide from an ion exchange chromatography material in a single step purification process, comprising the following two steps a) step one comprising the following sub-steps
- a1) providing a solution comprising a polypeptide, a buffer substance, and optionally a salt;
- a2) bringing a first aliquot of the solution containing the polypeptide and an ion exchange material in contact under conditions whereby the polypeptide binds to the ion exchange material;
- a3) recovering the polypeptide from the ion exchange material by using a solution comprising a buffer substance and a salt whereby the concentration of the salt is increased linearly;
- a4) determining the starting concentration of the salt where the first fraction of the polypeptide starts to elute from the ion exchange column;

b) step two comprising the following sub-steps
- b1) bringing a second aliquot of the solution containing the polypeptide and an ion exchange material in contact under conditions whereby the polypeptide binds to the ion exchange material;
- b2) recovering the polypeptide from the ion exchange material by using a three step elution method, whereby
  - i) the salt concentration of the first elution step is calculated as the sum of
    - the product of the starting concentration of the salt as determined in step a4) and the total number of monovalent cations different from hydrogen denoted in the molecular formula of the salt and
    - the product of the concentration of the buffer salt and the total number of monovalent cations different from hydrogen denoted in the molecular formula of the buffer salt;
  - ii) the salt concentration of the second elution step is the product of the salt concentration of the first elution step and a factor between 1.25 and 1.35;
  - iii) the salt concentration of the third elution step is the product of the salt concentration of the first elution step and a factor between 1.50 and 1.70;
  whereby the factors of step ii) and iii) are determined as follows: at a starting concentration between 10 mM and 40 mM the factors are 1.35 and 1.70 respectively, at a starting concentration between 40 mM and 70 mM the factors are 1.30 and 1.60 respectively, and at a staring concentrations of more than 70 mM the factors are 1.25 and 1.50 respectively.
- b3) determining at which sub-step of the three step elution method of step b2) the polypeptide is eluted from the ion exchange column thereby determining the concentration of a salt for eluting a polypeptide from an ion exchange chromatography material in a single step purification process.

The factors of step b2) define a range that has been determined experimentally. These values are no absolute values but merely a target value. A deviation of 10% is maintainable.

The current invention describes a method for determining the concentration of a salt for eluting a polypeptide from an ion exchange chromatography material in a single step purification process for the purification of polypeptides from other proteinaceous material.

The concentration, at which the elution of the polypeptide, preferably of an immunoglobulin, from the ion exchange resin starts, provides the basis for the second optimization step b), a three step elution method. The approximate buffer/salt concentrations for the step elution are calculated as follows:

the salt concentration of the first elution step is equal to the sum of
- as first summand the product of the concentration of the salt, at which the elution from the ion exchange column starts as determined with the linear increasing salt gradient, and the total number of monovalent cations different from hydrogen denoted in the molecular formula of the salt causing the elution and
- as second summand the product of the concentration of the buffer salt and the total number of monovalent cations different from hydrogen denoted in the molecular formula of the buffer salt;

the salt concentration of the second elution step is equal to the product of the salt concentration of the first elution step and a factor of between 1.25 and 1.35;

the salt concentration of the third elution step is equal to the product of the salt concentration of the first elution step and a factor between 1.50 and 1.70.

The factor included in the calculation of the concentration steps accounts for the interval between the concentration levels and is adjusted depending on the starting concentration. At small starting concentrations, i.e. between 10 mM and 40 mM, the factors are 1.35 and 1.70 respectively, at medium starting concentrations between 40 mM and 70 mM the factors are 1.30 and 1.60 respectively, and at high starting concentrations of more than 70 mM the factors are 1.25 and 1.50 respectively. These factors define a range that has been determined experimentally. These values are no absolute values but merely a target value. A deviation of 10% is maintainable.

The buffer salt has to be accounted for in the calculation because it is possible, as outlined in example 3, that the elution of a protein from an ion exchange resin can be effected by a change of the buffer salt concentration during the chromatography. If the buffer salt concentration is kept constant during the chromatography or is small compared to the stating concentration of the salt causing the elution it may be neglected during the calculation to reduce complexity.

In one embodiment the salt causing the elution is not the buffer salt and the salt concentration of step b2i) is the product of the concentration of the salt, at which the elution from the ion exchange column starts as determined with the linear increasing salt gradient in step a4), and the total number of monovalent cations different from hydrogen denoted in the molecular formula of the salt causing the elution.

The calculation will be exemplified based on example 4 with the anti IL-1R antibody. With a starting concentration of 15 mM sodium citrate, as determined in example 3, consisting of a 10 mM buffer concentration and a 5 mM contribution from the linear gradient, the three steps are calculated as follows:

the target concentration for step one is calculated to be 30 mM (5 mM*2+10 mM*2) sodium citrate
in detail: 5 mM (starting concentration) multiplied with two (citric acid is a trivalent acid, employed as di-sodium salt; therefore two monovalent cations different from hydrogen are present in the molecular formula) plus 10 mM (buffer salt concentration) multiplied with two (citric acid is a trivalent acid, employed as di-sodium salt; therefore two monovalent cations different from hydrogen are present in the molecular formula)

the target concentration for step two is calculated to be 40.5 mM (30 mM*1.35) sodium citrate
in detail: 30 mM sodium citrate is the concentration of step one multiplied by 1.35 (the starting concentration is 15 mM, therefore as factor 1.35 is selected)

the target concentration for step three is calculated to be 51 mM (30 mM*1.70) sodium citrate
in detail: 30 mM sodium citrate is the concentration of step one multiplied by 1.70 (the starting concentration is 15 mM, therefore as factor 1.70 is selected)

As can be seen from the experiments this purification is achieved in a preferred embodiment by the use of a weak ion exchange material, especially preferred of a weak cation exchange material.

A preferred embodiment of the invention is that the polypeptide is an immunoglobulin, especially preferred an immunoglobulin of the IgG or IgE class.

In one embodiment of the invention the pH value of the buffer material/substance is of from pH 3.0 to pH 10.0, preferably of from pH 3.0 to pH 7.0, more preferred of from pH 4.0 to pH 6.0 and most preferred of from pH 4.5 to pH 5.5.

Another preferred item of the current invention is that the method of the current invention is applicable to immunoglobulins that have an isoelectric point (pI) of 6.0 or more (pI≥6.0) and therefore have a net positive charge in the pH range starting from pH 6.0 to pH 14.

The buffer material/substance is preferably employed in a concentration range between 5 mM and 100 mM as exemplified.

For the recovering of the bound immunoglobulins from the ion exchange material the conductivity of the buffer/solution is increased. This can be accomplished either by an increased buffer salt concentration or by the addition of other salts, so called elution salts, to the buffer solution. Preferred elution salts are sodium citrate, sodium chloride, sodium sulphate, sodium phosphate, potassium chloride, potassium sulfate, potassium phosphate, as well as other salts of citric and phosphoric acid, and any mixture of these components. Especially preferred are sodium citrate, sodium chloride, potassium chloride and any mixture thereof.

The concentration of the salt, causing the elution, is preferably in the range of between 5 mM and 500 mM, more preferred between 5 mM and 400 mM, and especially preferred between 5 mM and 250 mM.

Another preferred embodiment of the invention is the use of the salt, causing the elution, at the same time as buffer substance, especially with citric acid and salts thereof or phosphoric acid and salts thereof.

The method of the current invention is preferably a chromatographic or batch method, especially preferred is a method comprising a batch elution.

Another preferred embodiment of the current invention is that the purification is a single step purification process.

Still a preferred embodiment of the current invention is that the method comprises the additional step of a purification of the immunoglobulin by a protein A affinity chromatography before step a) of the method.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 5 Single step gradient elution of anti IL-1R antibody from weak cation exchange resin CM-Sepharose with 150 mM sodium chloride at pH 5.5; monomeric and aggregated forms of the receptor antibody are separated and elute as a main peak comprising the monomeric form of the immunoglobulin and as a second peak, comprising monomeric and aggregated forms of the immunoglobulin as well as protein A.

FIG. 6b Elution profile of anti IL-1R antibody on a SP-Sepharose fast flow; one peak can be identified which contains monomeric immunoglobulin, aggregates and other impurities which have not been separated on this column.

FIG. 8a Single step gradient elution of anti IL-1R antibody from weak cation exchange resin CM-Sepharose with 150 mM sodium chloride at pH 4.0.

FIG. 8b Single step gradient elution of anti IL-1R antibody from weak cation exchange resin CM-Sepharose with 150 mM sodium chloride at pH 6.0.

FIG. 10 Single step elution of anti-HER-2 antibody from strong cation exchange resin SP-Sepharose; monomeric and aggregated forms of the antibody are not separated and elute as one peak.

FIG. 11 Linear gradient elution of anti-HER-2 antibody from weak cation exchange resin CM-Sepharose with sodium chloride in sodium citrate buffer at pH 5.5; monomeric and aggregated forms of the antibody are partially separated and elute with a starting concentration of 80 mM sodium chloride as one main peak comprising the monomeric form of the immunoglobulin; the monomeric and aggregated forms elute as mixture in the tailing of the main peak together with protein A.

EXPERIMENTAL PART

Material:

An IgG4 immunoglobulin anti IL-1R antibody (hereinafter referred to as immunoglobulin, WO 2005/023872) was purified in a first step with a protein A affinity chromatography. Elution from the protein A column was carried out under acidic conditions (10 mM sodium citrate buffer, pH value 3.0±0.5). Before the filtration step the pH value of the fraction containing the immunoglobulin was adjusted with a concentrated, e.g. 1 M, buffer solution of pH 9.0 (e.g. tris-hydroxymethyl-aminomethane (TRIS) or phosphate buffer) to pH 5.0. The protein A eluate is a solution with a protein concentration between 5 mg/ml and 15 mg/ml and is buffered with sodium citrate. This material is referred to in the following as conditioned protein A eluate, which is prepared for loading onto a cationic exchange resin.

Example 1

In this comparative example an ion exchange chromatography with a strong cation exchange resin and single step elution is described.

Chromatographic Conditions:
Resin: SP-Sepharose
Flow rate: 160 cm/h
Equilibration: 10 mM sodium citrate buffer, adjusted to pH 5.0
Loading: max. 20 g protein/L gel matrix
Wash step: 10 mM sodium citrate buffer, adjusted to pH 5.0
Elution: 25 mM sodium citrate buffer with 100 mM sodium chloride, adjusted to pH 5.0

The conditioned protein A eluate was applied to a chromatography column containing a strong cation exchange resin (SP-Sepharose). After the loading step at a flow rate of 160 cm/h the column was washed with equilibration buffer (10 column volumes). The bound immunoglobulins were eluted with a single step elution method, whereby the pH value was kept constant and the conductivity was varied (increased) by the addition of sodium chloride.

Figure 1:
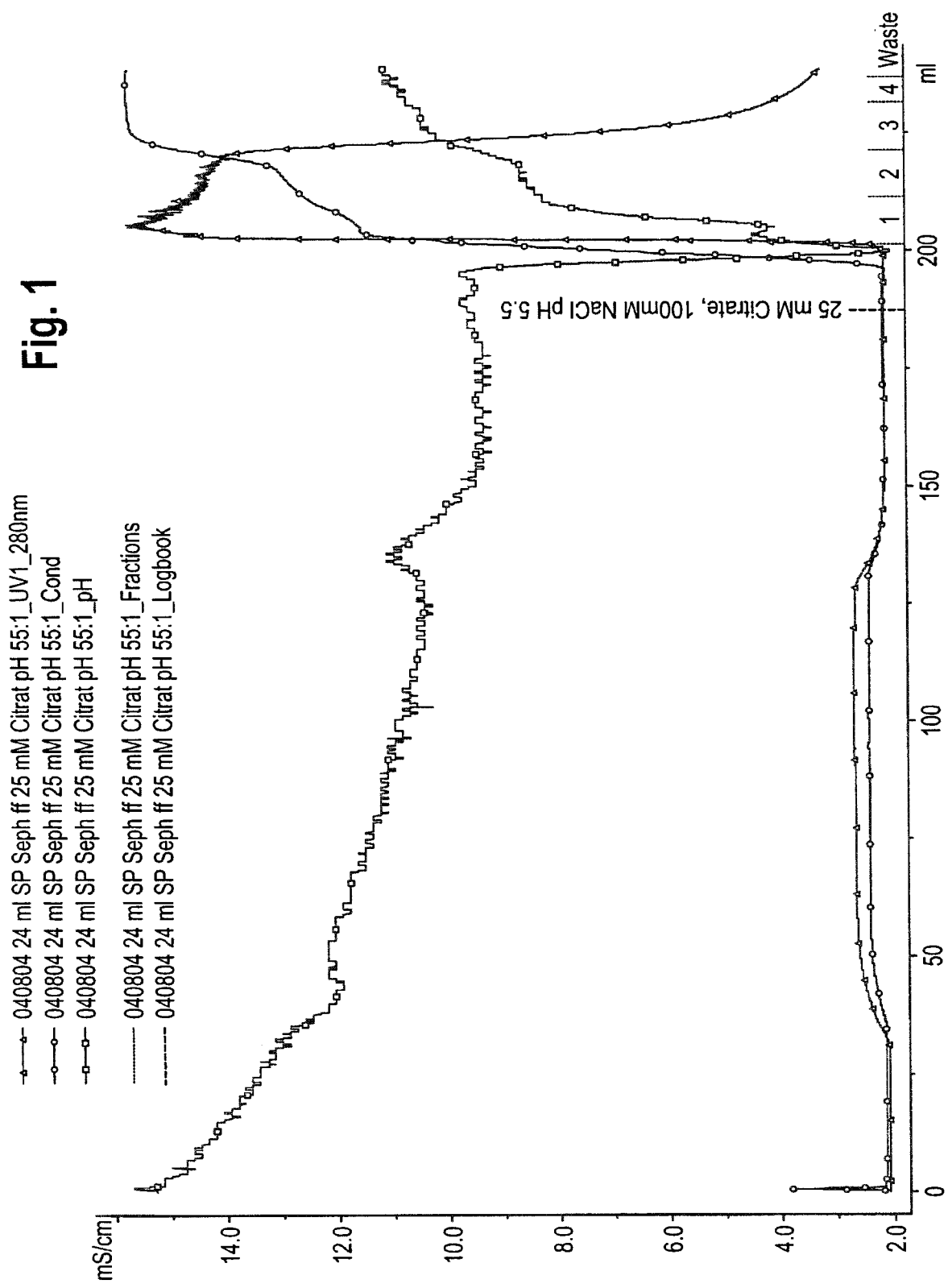
FIG. 1 Single step elution of anti IL-1R antibody from strong cation exchange resin SP-Sepharose; monomeric and aggregated forms of the receptor antibody are not separated and elute as one peak.

In FIG. 1 the elution chromatogram of the cation exchange chromatography of the anti IL-1R antibody on the strong cation exchange resin SP-Sepharose is presented. The elution is a single step replacement elution with sodium chloride without altering the pH value of the chromatographic system. The monomeric and aggregated immunoglobulin molecules are not separated and thus with this method no purification by reduction of the aggregate content in the eluate compared to the loaded material can be obtained.

Example 2

In this example an ion exchange chromatography with a weak cation exchange resin and single step elution is described.

To achieve a separation of monomeric and aggregated forms of an immunoglobulin, a weak cation exchange resin was employed. By using this kind of resin an increase of the conductivity by a step elution is accompanied by a particular pH shift on the resin (even when the pH of the eluting buffer remains constant). This effect facilitates the discrimination e.g. between monomeric immunoglobulins and aggregated forms. Furthermore, other impurities, like traces of host cell proteins or protein A, can efficiently be separated from the monomeric mean fraction, without significant loss in yield.

Chromatographic Conditions:
Resin: CM-Toyopearl
Flow rate: 160 cm/h
Equilibration: 10 mM sodium citrate buffer, adjusted to pH 5.0
Loading: max. 20 g protein/L gel matrix
Wash: 10 mM sodium citrate buffer, adjusted to pH 5.0
Elution: 25 mM sodium citrate buffer with 100 mM sodium chloride, adjusted to pH 5.0

The conditioned protein A eluate was applied to a chromatography column containing a weak cation exchange resin (CM-Toyopearl). After the loading step at a flow rate of 160 cm/h the column was washed with equilibration buffer (10 column volumes). The bound immunoglobulins were eluted with a single step elution method, whereby the pH value in the mobile phase was kept constant and the conductivity was varied by the addition of sodium chloride.

Figure 2:
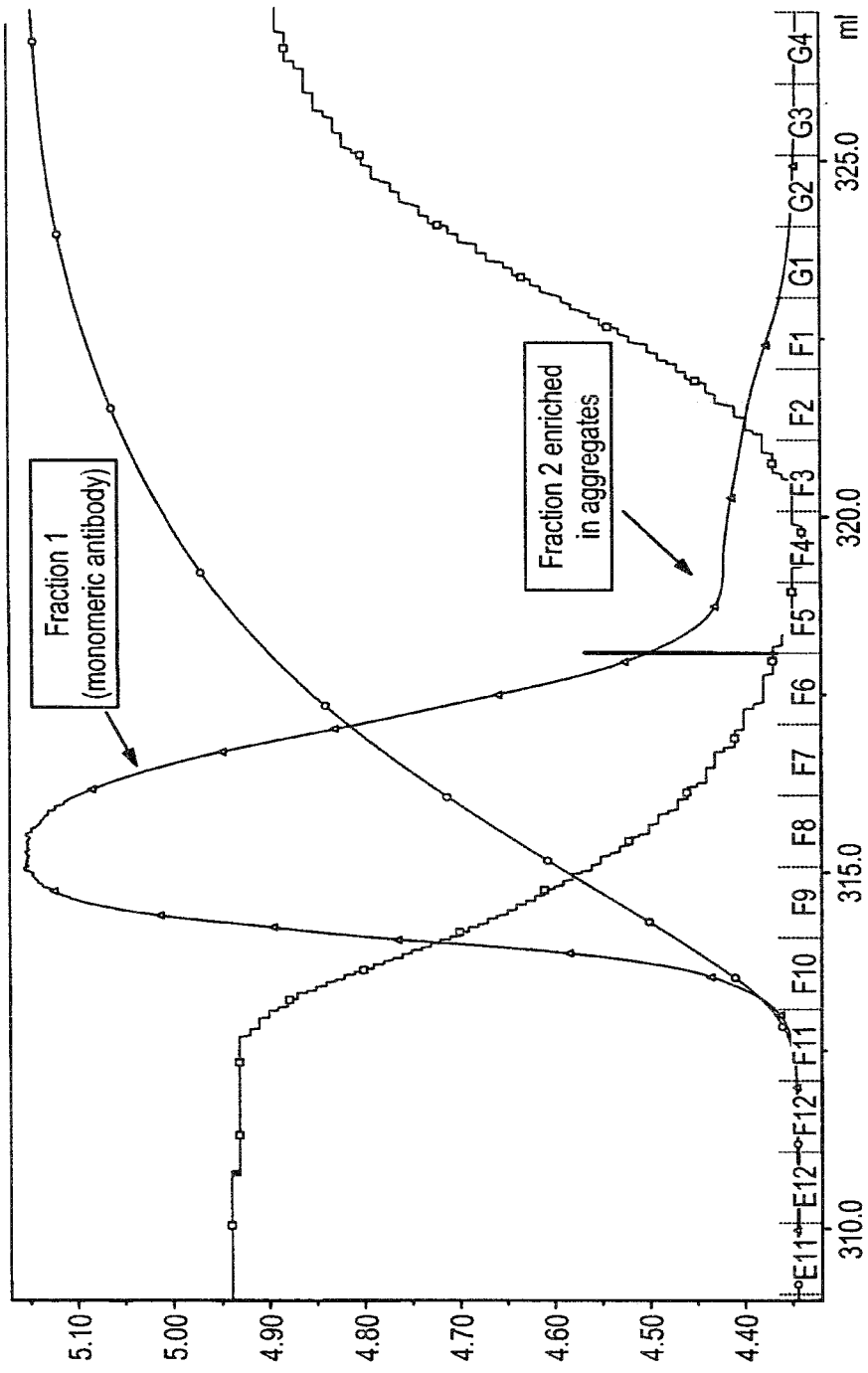
FIG. 2 Single step elution of anti IL-1R antibody from weak cation exchange resin CM-Toyopearl; monomeric and aggregated forms of the receptor antibody are partially separated and elute as one main peak comprising the monomeric form of the immunoglobulin and as a second peak, comprising monomeric and aggregated forms of the immunoglobulin as well as protein A.
Figure 9A:
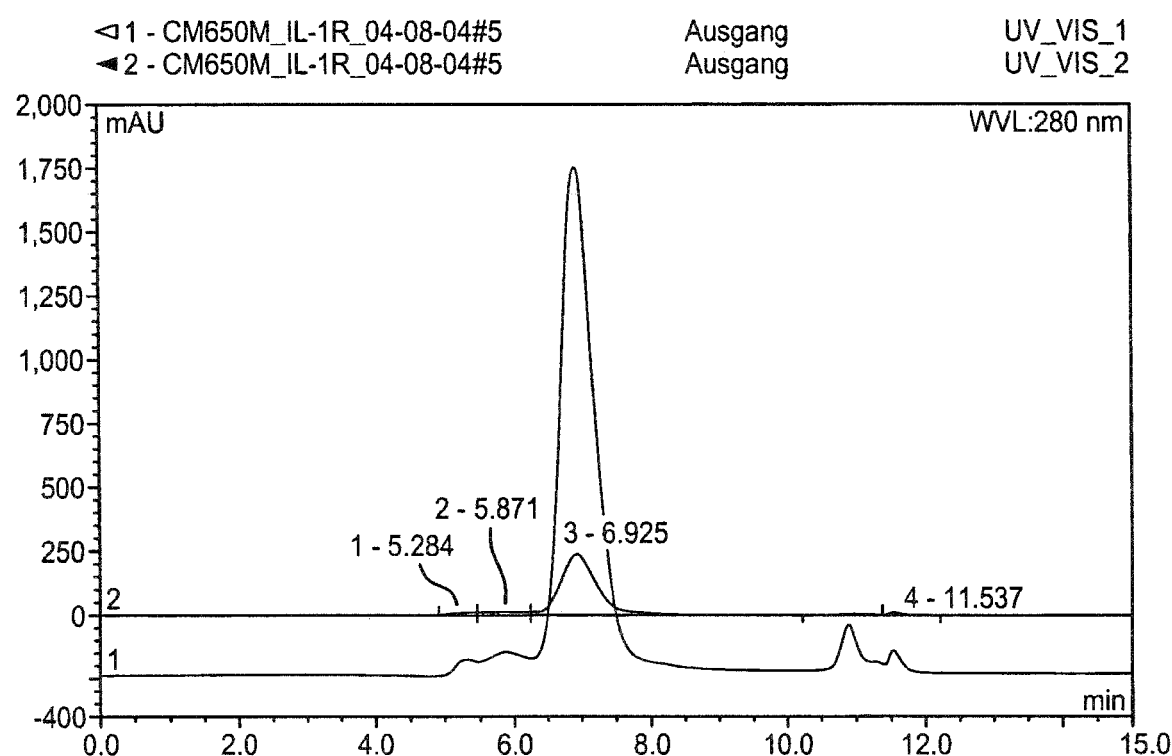
FIG. 9a Single step elution of anti IL-1R antibody from weak cation exchange resin CM-Sepharose; size exclusion chromatography (SEC) of the starting material showing both monomeric and aggregated forms of the immunoglobulin.
Figure 9B:
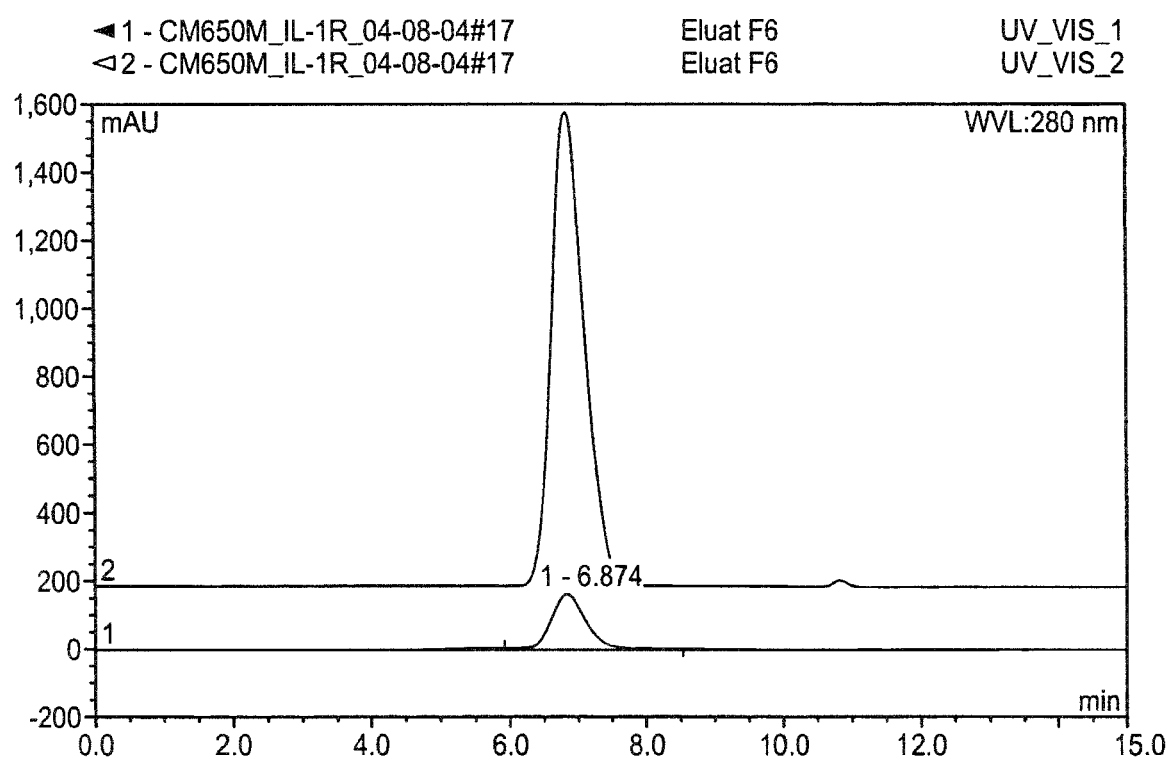
FIG. 9b Single step elution of anti IL-1R antibody from weak cation exchange resin CM-Sepharose; monomeric and aggregated forms of the receptor antibody are partially separated and elute as one main peak comprising the monomeric form of the immunoglobulin and as a second peak, comprising monomeric and aggregated forms of the immunoglobulin as well as other protein. In this figure the size exclusion chromatography of the first (main) peak is shown. Only one peak is eluted from the SEC-column, which is the monomeric immunoglobulin.
Figure 9C:
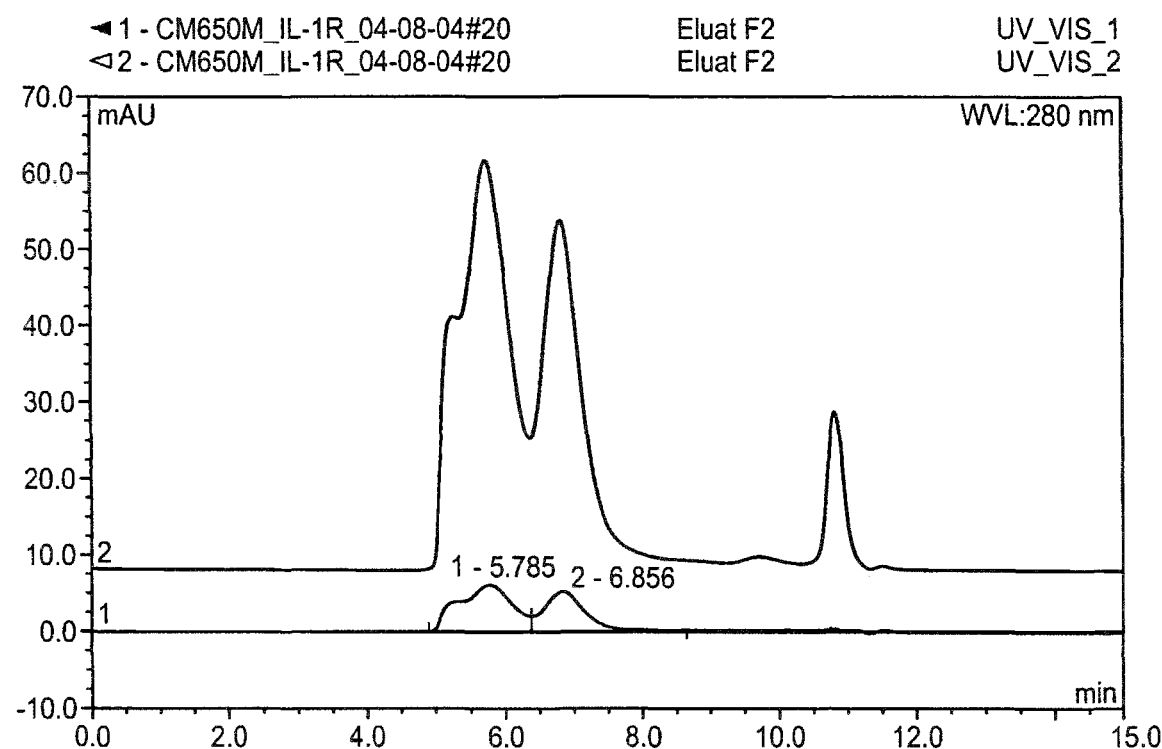
FIG. 9c Single step elution of anti IL-1R antibody from weak cation exchange resin CM-Sepharose; monomeric and aggregated forms of the receptor antibody are partially separated and elute as one main peak comprising the monomeric form of the immunoglobulin and as a second peak, comprising monomeric and aggregated forms of the immunoglobulin as well as other protein. In this figure the size exclusion chromatography of the second peak is shown. In the chromatogram at least three peaks can be seen, equivalent to monomeric and aggregated forms of the immunoglobulin and other protein.

In FIG. 2 the elution profile with the same chromatographic conditions as in example 1 but this time with a weak cation exchange resin, CM-Toyopearl, is presented. Herein a second peak as shoulder of the main peak appears. This separation behavior is different to that with a strong cation exchange resin, such as SP-Sepharose. An analysis of fractions corresponding to the main peak and to the second shoulder peak showed a significant amount of aggregates to be present in the shoulder peak fraction. No aggregates were detectable in the main peak fractions (see also FIGS. 9a to c).

Example 3

Optimization of the Chromatographic Method—First Step: Linear Concentration Gradient.

To optimize the cation exchange chromatography on a weak cation exchange material an optimization procedure, which is consisting of three steps, was put into practice:

The first step is a chromatography using a linear concentration gradient of the buffer salt, sodium citrate. Just as well is it possible to keep the concentration of the buffer salt constant and to admix a linearly increasing concentration of a salt causing the elution of the immunoglobulin. In both cases is the conductivity of the solution increased without an alteration of the pH value of the mobile phase. Salts suitable for the elution are e.g. sodium chloride, sodium sulphate, sodium phosphate, potassium chloride, potassium sulfate, potassium phosphate, citric acid and salts thereof as well as mixtures of these components. The concentrations of from 10 mM to 500 mM, which are applied, are adjusted accordingly to set conductivity in the range of from about 1 milli S/cm to about 50 milli S/cm.

Chromatographic Conditions:
Resin CM-Toyopearl
Flow rate: 160 cm/h
Equilibration: 10 mM sodium citrate buffer, adjusted to pH 5.0
Loading: max. 20 g protein/L gel matrix
Wash: 10 mM sodium citrate buffer, adjusted to pH 5.0
Elution: linear gradient; from 10 mM sodium citrate buffer, adjusted to pH 5.0, to 100 mM sodium citrate buffer, adjusted to pH 5.0

The conditioned protein A eluate was applied to a chromatography column containing a weak cation exchange resin (CM-Toyopearl). After the loading step at a flow rate of 160 cm/h the column was washed with equilibration buffer (10 column volumes). The bound immunoglobulins were eluted with a linear gradient elution method, whereby the pH value in the mobile phase was kept constant. The concentration of the buffer salt, sodium citrate, was raised linearly from 10 mM to 100 mM over 40 column volumes. After the final sodium citrate concentration was reached the elution was continued for an additional 40 column volumes.

Figure 3:
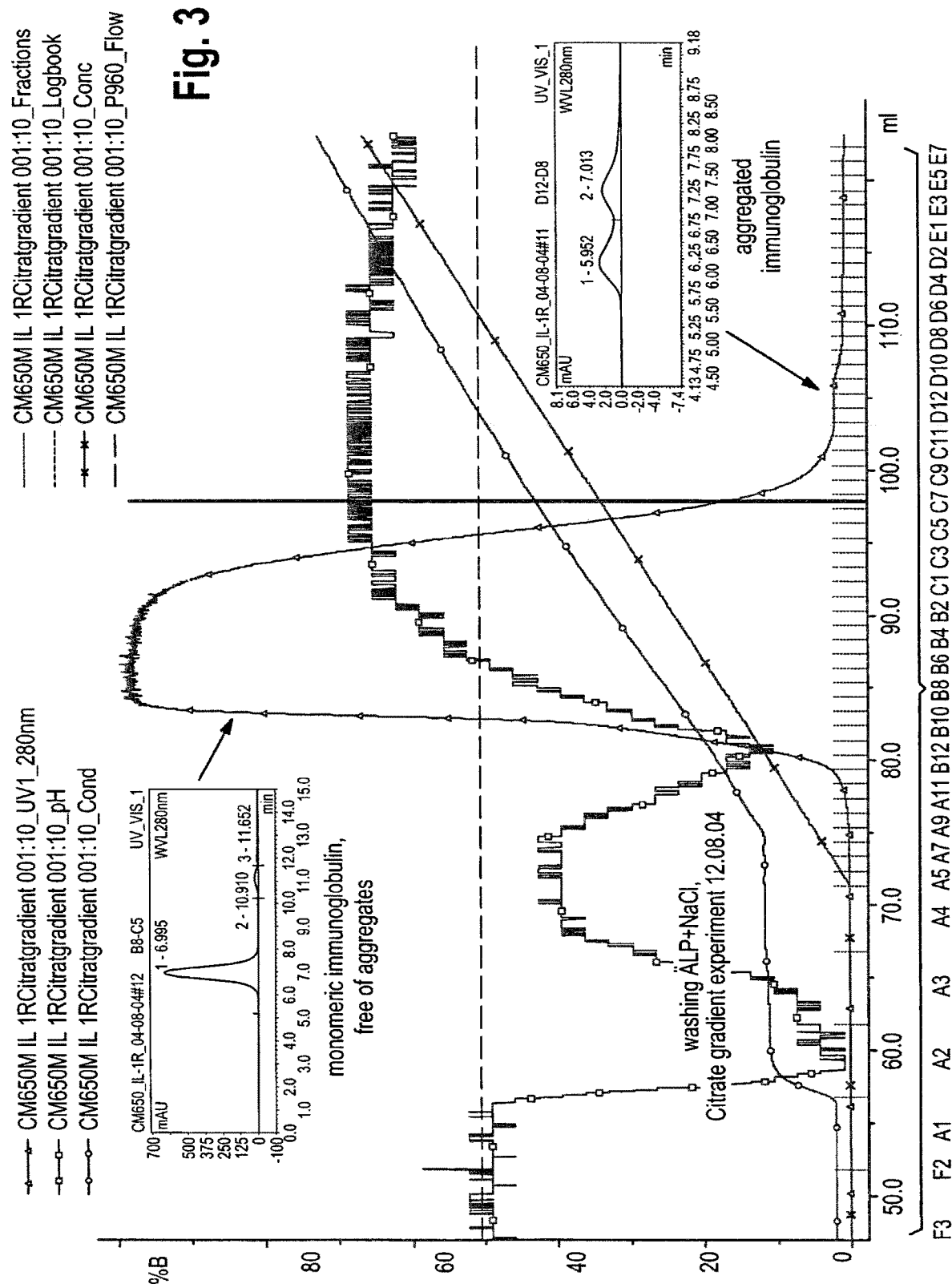
FIG. 3 Linear gradient elution of anti IL-1R antibody from weak cation exchange resin CM-Toyopearl with sodium citrate at pH 5.0; monomeric and aggregated forms of the receptor antibody are partially separated and elute at a sodium citrate starting concentration of 15 mM as a main peak comprising the monomeric form of the immunoglobulin and as a second peak, comprising a mixture of monomeric form, aggregated forms of the immunoglobulin, and protein A. The SEC analysis of the two fractions is inserted into the ion exchange chromatogram. In the main peak aggregates are absent. In contrast in the second peak aggregated forms of the immunoglobulin are present.

In FIG. 3 the chromatogram of the linear buffer gradient elution of the anti IL-1R antibody is presented. The monomeric and the aggregated form of the immunoglobulin elute in a semi-detached peak starting at a concentration of 15 mM sodium citrate and ending at a concentration of 55 mM sodium citrate.

The recovery of the bound immunoglobulin from the cation exchange resin is depending on the conductivity of the applied solution. Therefore the cations of the buffer salt present in the eluting solution during the recovery step have to be considered as effecting the elution of the immunoglobulin from the cation exchange resin. The conductivity as well as the ionic strength of the mobile phase are effected by the total number of ions in the solution. Thus the number of monovalent cations different from hydrogen in one molecular formula of the employed buffer salt and the employed salt causing the elution have to be considered hereby.

Example 4

Optimization of the Chromatographic Method—Second Step: Three Step Concentration Gradient Elution.

The concentration, at which the elution of the immunoglobulin from the ion exchange resin starts, as determined in example 3, provides the basis for the second optimization step, a three step elution method. The approximate buffer/salt concentrations for the step elution are calculated as follows:

the salt concentration of the first elution step is equal to the sum of as first summand the product of the concentration of the salt, at which the elution from the ion exchange column starts as determined with the linear increasing salt gradient, and the total number of monovalent cations different from hydrogen denoted in the molecular formula of the salt causing the elution and as second summand the product of the concentration of the buffer salt and the total number of monovalent cations different from hydrogen denoted in the molecular formula of the buffer salt;

the salt concentration of the second elution step is equal to the product of the salt concentration of the first elution step and a factor of between 1.25 and 1.35;

the salt concentration of the third elution step is equal to the product of the salt concentration of the first elution step and a factor between 1.50 and 1.70.

The factor included in the calculation of the concentration steps accounts for the interval between the concentration levels and is adjusted depending on the starting concentration. At small starting concentrations, i.e. between 10 mM and 40 mM, the factors are 1.35 and 1.70 respectively, at medium starting concentrations between 40 mM and 70 mM the factors are 1.30 and 1.60 respectively, and at high starting concentrations of more than 70 mM the factors are 1.25 and 1.50 respectively.

The factors define a range that has been determined experimentally. These values are no absolute values but merely a target value. A deviation of 10% is maintainable.

The buffer salt has to be accounted for in the calculation because it is possible as outlined in example 3 that the elution of a protein from an ion exchange resin can be effected by a change of the buffer salt concentration during the chromatography. If the buffer salt concentration is kept constant during the chromatography or is small compared to the stating concentration ($\leq 15\%$ of the salt concentration) it may be neglected during the calculation to reduce complexity.

With a starting concentration of 15 mM sodium citrate, as determined in example 3, consisting of a 10 mM buffer concentration and a 5 mM contribution from the linear gradient, the three steps can be calculated as follows:
- the target concentration for step 1 is calculated to be 30 mM (5 mM*2+10 mM*2) sodium citrate
  - in detail: 5 mM (starting concentration) multiplied with two (citric acid is a trivalent acid, employed as di-sodium salt; therefore two monovalent cations different from hydrogen are present in the molecular formula) plus 10 mM (buffer salt concentration) multiplied with two (citric acid is a trivalent acid, employed as di-sodium salt; therefore two monovalent cations different from hydrogen are present in the molecular formula)
- the target concentration for step 2 is calculated to be 40.5 mM (30 mM*1.35) sodium citrate
  - in detail: 30 mM sodium citrate is the concentration of step 1 multiplied by 1.35 (the starting concentration is 15 mM, therefore as factor 1.35 is selected)
- the target concentration for step 3 is calculated to be 51 mM (30 mM*1.70) sodium citrate
  - in detail: 30 mM sodium citrate is the concentration of step 1 multiplied by 1.70 (the starting concentration is 15 mM, therefore as factor 1.70 is selected)

Chromatographic Conditions:
Resin: CM-Toyopearl
Flow rate: 160 cm/h
Equilibration: 10 mM sodium citrate buffer, adjusted to pH 5.0
Loading: max. 20 g protein/L gel matrix
Wash: 10 mM sodium citrate buffer, adjusted to pH 5.0
Elution: step 1: 34 mM sodium citrate buffer, adjusted to pH 5.0
  step 2: 44 mM sodium citrate buffer, adjusted to pH 5.0
  step 3: 54 mM sodium citrate buffer, adjusted to pH 5.0

The conditioned protein A eluate was applied to a chromatography column containing a weak cation exchange resin (CM-Toyopearl). After the loading step at a flow rate of 160 cm/h the column was washed with equilibration buffer (10 column volumes). The bound immunoglobulins were eluted with a step gradient elution method (=a method wherein the concentration of the elution salt is changed stepwise from a starting value/level to a final value/level), whereby the pH value in the mobile phase was kept constant. The concentration of the buffer salt, sodium citrate, was raised from 10 mM as starting condition to 34 mM in the first step, to 44 mM in the second step, and to 54 mM in the final step. After each increase of the salt concentration ten column volumes of the elution buffer were passed through the column prior to the next step. After the final sodium citrate concentration was reached the elution was continued for an additional 10 column volumes.

Figure 4:
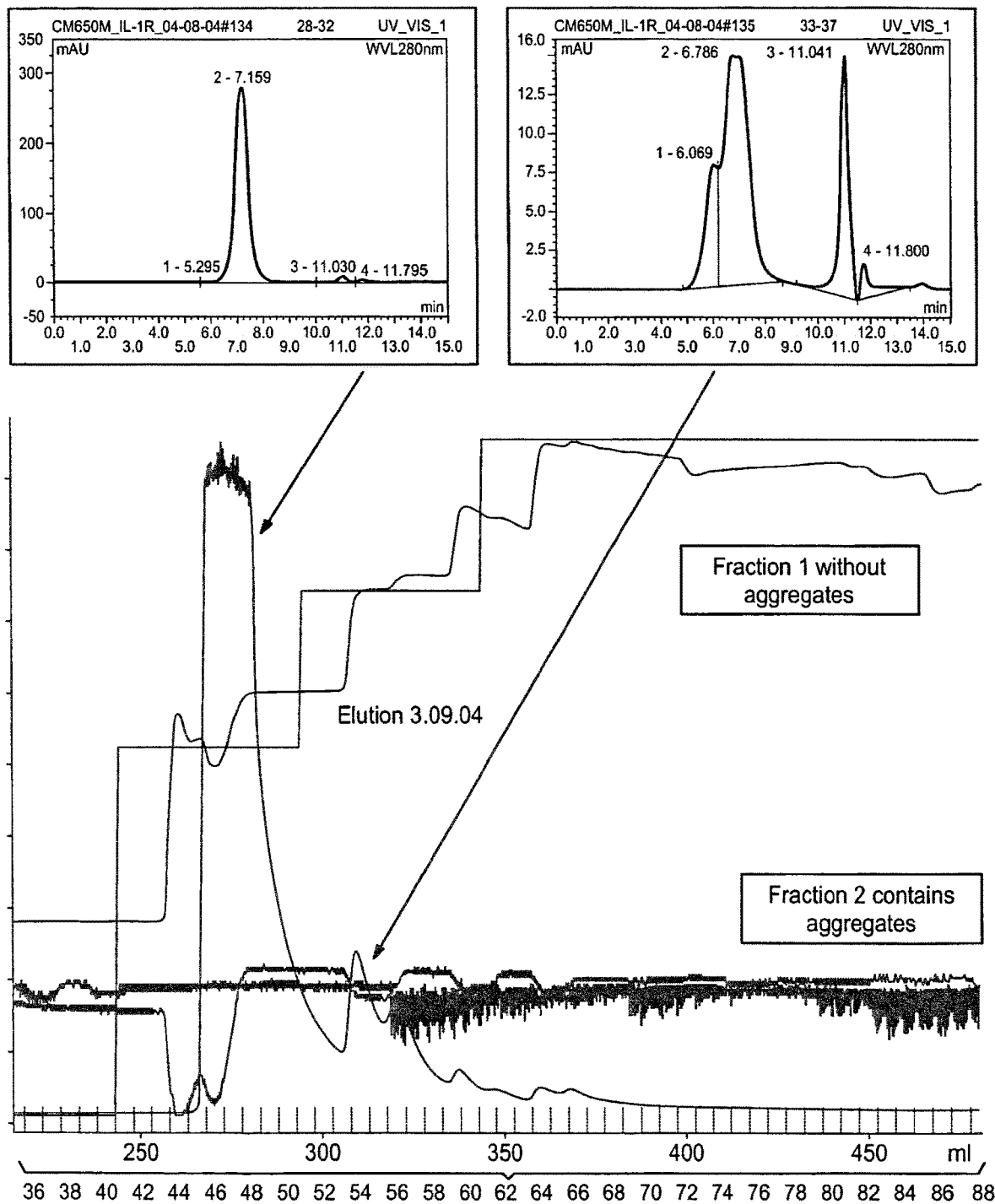
FIG. 4 Three step gradient elution of anti IL-1R antibody from weak cation exchange resin CM-Toyopearl with sodium citrate at pH 5.0; monomeric and aggregated forms of the receptor antibody are partially separated and elute as a main peak comprising the monomeric form of the immunoglobulin at a sodium citrate concentration of 34 mM and as a second peak, comprising monomeric and aggregated forms of the immunoglobulin as well as protein A at a sodium citrate concentration of 44 mM.

In FIG. 4 the elution profile of the three step gradient elution of anti IL-1R antibody is presented. The monomeric immunoglobulin elutes in the first step fraction and the aggregates elute in the second step fraction.

Example 5

Optimization of the Chromatographic Method—Third Step: Single Step Elution with Sodium Chloride.

The final step of the optimization procedure is the adaptation to a single step elution method (=a method wherein the concentration of the elution salt is changed at once from a starting value to a final value). For this purpose the pH of the chromatography is raised from 5.0 to 5.5. This pH shift improves the separation from protein A, due that protein A has an isoelectric point below 5.5. Additionally the elution salt is changed from sodium citrate, which is further on used as buffer salt, to sodium chloride. Additional analyses have been carried out (DNA, host cell protein, protein A content, and glycosylation pattern with LC-MS) with the fractions after this chromatographic run.

Chromatographic Conditions:
Resin: CM-Sepharose
Flow rate: 160 cm/h
Equilibration: 10 mM sodium citrate, adjusted to pH 5.5
Loading: max. 20 g protein/L gel matrix
Wash: 10 mM sodium citrate, adjusted to pH 5.5
Elution: 10 mM sodium citrate with 150 mM sodium chloride, adjusted to pH 5.5

The conditioned protein A eluate was applied to a chromatography column containing a weak cation exchange resin (CM-Sepharose). After the loading step at a flow rate of 160 cm/h the column was washed with equilibration buffer (10 column volumes). The bound immunoglobulins were eluted with a single step gradient elution method (=a method wherein the concentration of the elution salt is changed at once from a starting value to a final value), whereby the pH value in the mobile phase was kept constant. The concentration of the buffer salt, sodium citrate, was kept constant and 150 mM sodium chloride was admixed. After the increase of the salt concentration fifteen column volumes of the elution buffer were passed through the column to elute the bound immunoglobulin.

The elution chromatogram of the single step elution with sodium chloride is presented in FIG. 5. The single step gradient chromatography effects resolution of the main monomeric fraction and the aggregate/protein A fraction. The yield of monomeric immunoglobulin is more than 80%. Even more than 95% yield is possible.

Example 6

Comparison Between the Separation with a Strong Cation Exchange Resin (SP-Sepharose Fast Flow) and a Weak Cation Exchange Resin (CM-Sepharose Fast Flow).

Figure 6A:
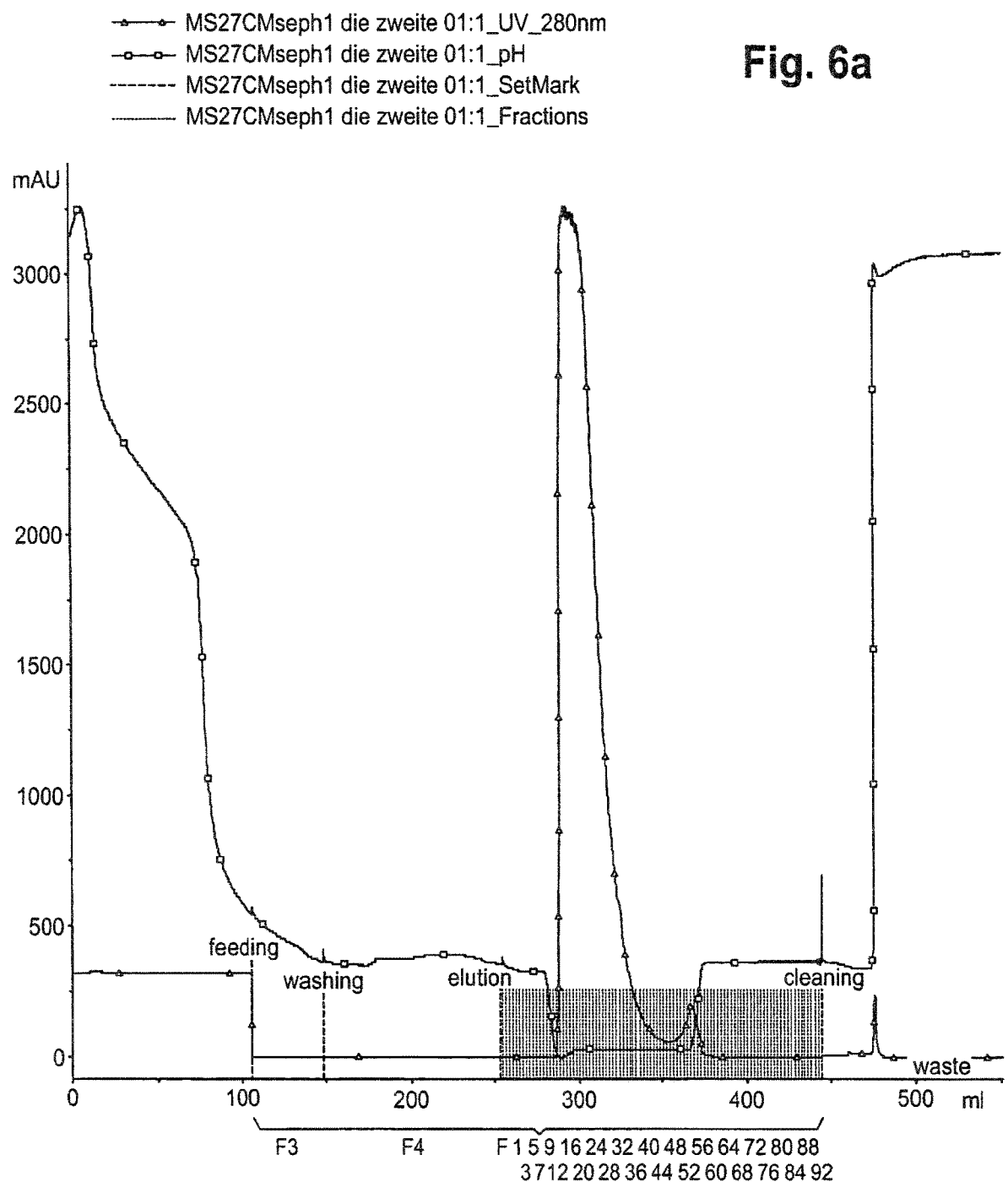
FIG. 6a Elution profile on a CM-Sepharose fast flow; two peaks can be identified: a main peak, corresponding to the monomeric anti IL-1R antibody, and a smaller second peak, that contains mainly aggregates and other impurities.

A comparison between the strong SP-Sepharose ff exchanger and CM-Sepharose ff was done. Experiments were performed according to example 5 in duplicates (only one from each column is shown in FIGS. 6a and b) and additional analyses have been carried out (DNA, host cell protein, protein A content, and glycosylation pattern with LC-MS).

Analytical Methods:

| | | |
|---|---|---|
| Size Exclusion Chromatography: | resin: | TSK 3000 (Tosohaas) |
| | column: | 300 × 7.8 mm |
| | flow rate: | 0.5 ml/min |
| | buffer: | 200 mM potassium phosphate containing 250 mM potassium chloride, adjusted to pH 7.0 |
| DNA-threshold-system: | see e.g. Merrick, H., and Hawlitschek, G., Biotech Forum Europe 9 (1992) 398-403 | |
| Protein A ELISA: | The wells of a micro titer plate are coated with a polyclonal protein A-IgG derived from chicken. After binding non-reacted antibody is removed by washing with sample buffer. For protein A binding a defined sample volume is added to the wells. The protein A present in the sample is bound by the chicken antibody and retained in the wells of the plate. After the incubation the sample solution is removed and the | |

-continued

| | |
|---|---|
| | wells are washed. For detection are added subsequently a chicken derived polyclonal anti-protein A-IgG-biotin conjugate and a streptavidin peroxidase conjugate. After a further washing step substrate solution is added resulting in the formation of a colored reaction product. The intensity of the color is proportional to the protein A content of the sample. After a defined time the reaction is stopped and the absorbance is measured. |
| Host cell protein (HCP) ELISA: | The walls of the wells of a micro titer plate are coated with a mixture of serum albumin and streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm. |

Chromatographic Conditions:
Resin: CM-Sepharose; SP-Sepharose
Flow rate: 160 cm/h
Equilibration: 10 mM sodium citrate buffer, adjusted to pH 5.5
Loading: max. 20 g protein/L gel matrix
Wash: 10 mM sodium citrate buffer, adjusted to pH 5.5
Elution: 10 mM sodium citrate buffer with 150 mM sodium chloride, adjusted to pH 5.5

In FIGS. 6a and 6b a comparison between the elution chromatogram of a weak and a strong cation exchange resin is presented. Using a weak cation exchange resin (FIG. 6a) a separation of the monomeric anti IL-1R antibody from other impurities is achieved. With the strong cation exchange resin (FIG. 6b) no separation is possible under the same conditions. The fractions corresponding to the peaks have been collected and analyzed. The analysis results, which are listed in table 1, show that with the weak cation exchange resin aggregates and other impurities can effectively be depleted from the immunoglobulin preparation.

The data presented in table 1 show that it is possible to separate with a weak cation exchange resin monomeric anti IL-1R antibody from aggregated forms of the antibody. Furthermore DNA- and protein A-impurities can be depleted.

TABLE 1

Analysis of the eluates: comparison between SP-Sepharose and CM-Sepharose, results of two different separations are presented.

| analyte | conditioned protein A eluate | SP-Sepharose eluate single peak | | CM-Sepharose eluate | | | |
|---|---|---|---|---|---|---|---|
| | | | | Peak 1 | | Peak 2 | |
| amount of protein A | between 20 and 50 ng/mg | 31 ng/mg | 26 ng/mg | 7.5 ng/mg | 11 ng/mg | 1638 ng/mg | 550 ng/mg |
| HCP | between 20 ng/mg and 120 ng/mg | 3.88 ng/mg | 3.98 ng/mg | 3.13 ng/mg | 3.27 ng/mg | 946 ng/mg | 1424 ng/mg |
| DNA | between 2800 and 3500 pg/mg | 36 pg/mg | 16 pg/mg | 157 pg/mg | 131 pg/mg | 1918 pg/mg | 1222 pg/mg |
| aggregates | present | present | present | not present | not present | present in high amount | present in high amount |
| mass analysis | no differences were found between SP- and CM-Sepharose | | | | | | |

Example 7

Comparative Example—Elution at Different Conductivities

Chromatographic Conditions:
Resin: CM-Sepharose
Flow rate: 160 cm/h
Equilibration: 10 mM sodium citrate buffer, adjusted to pH 5.5
Loading: max. 20 g protein/L gel matrix
Wash: 10 mM sodium citrate buffer, adjusted to pH 5.5
Elution: 10 mM sodium citrate buffer with 100 mM, 150 mM or 200 mM sodium chloride, adjusted to pH 5.5

Figure 7A:
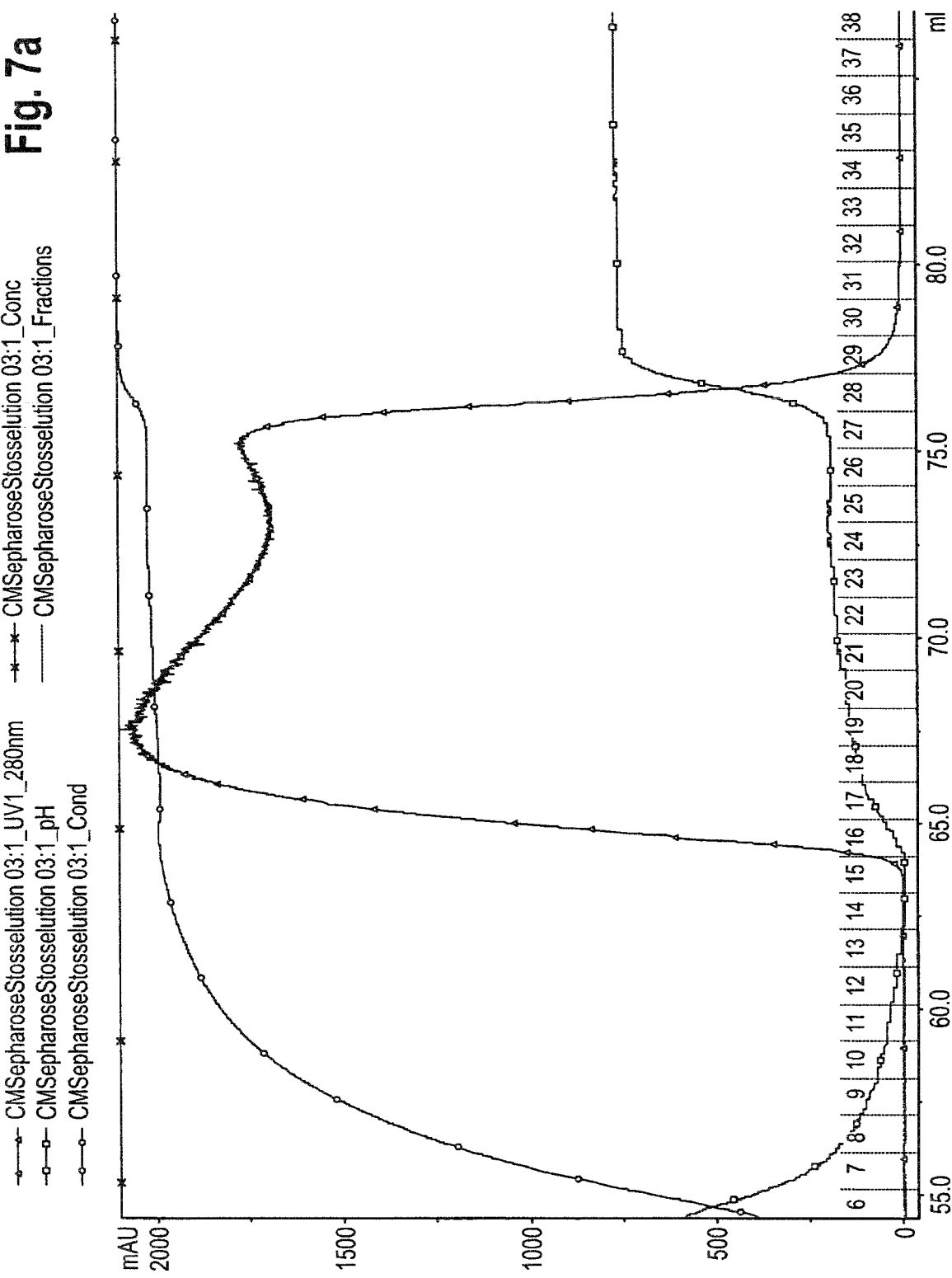
FIG. 7a Single step gradient elution of anti IL-1R antibody from weak cation exchange resin CM-Sepharose with 100 mM sodium chloride at pH 5.5.
Figure 7B:
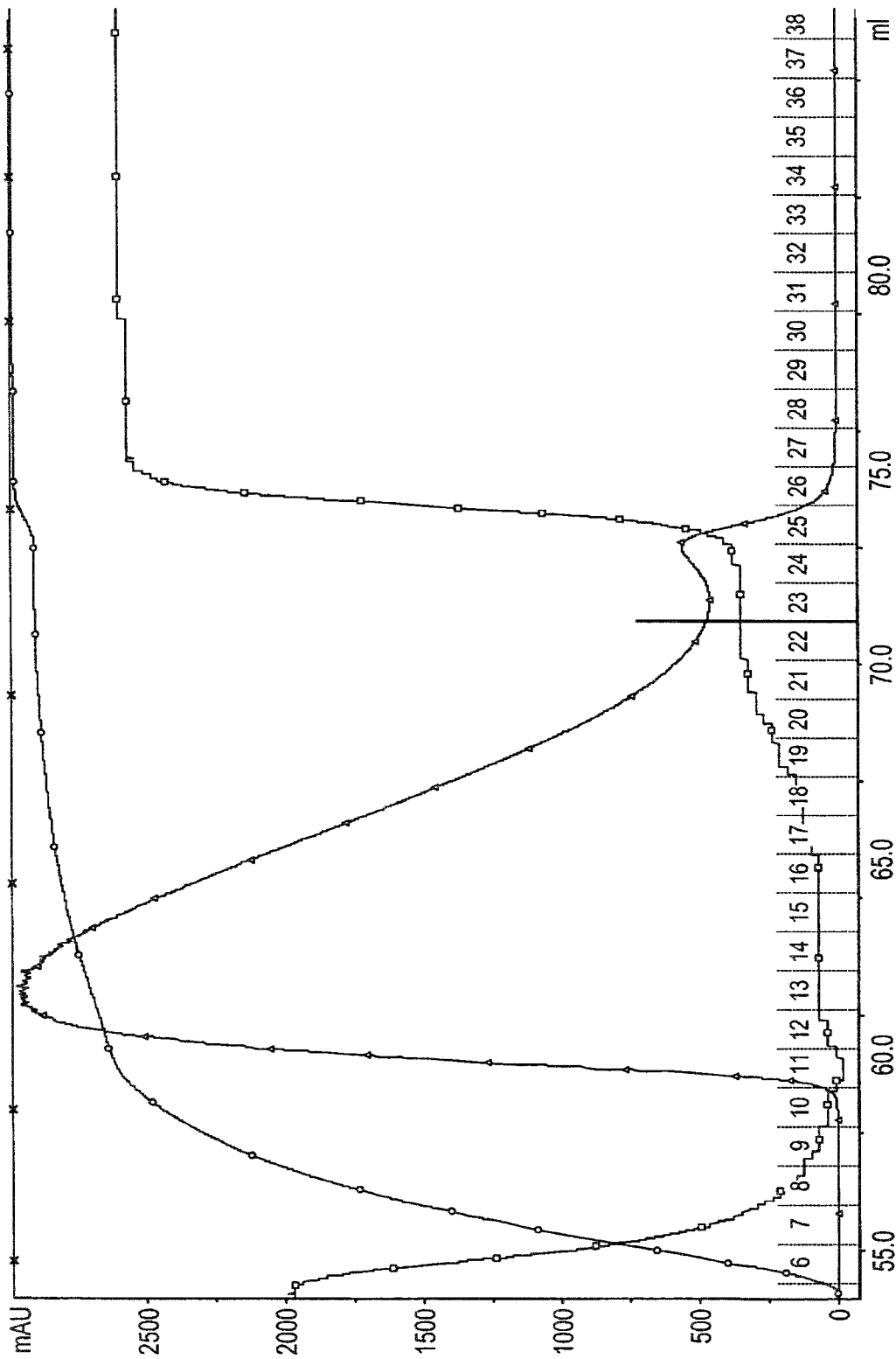
FIG. 7b Single step gradient elution of anti IL-1R antibody from weak cation exchange resin CM-Sepharose with 150 mM sodium chloride at pH 5.5.
Figure 7C:
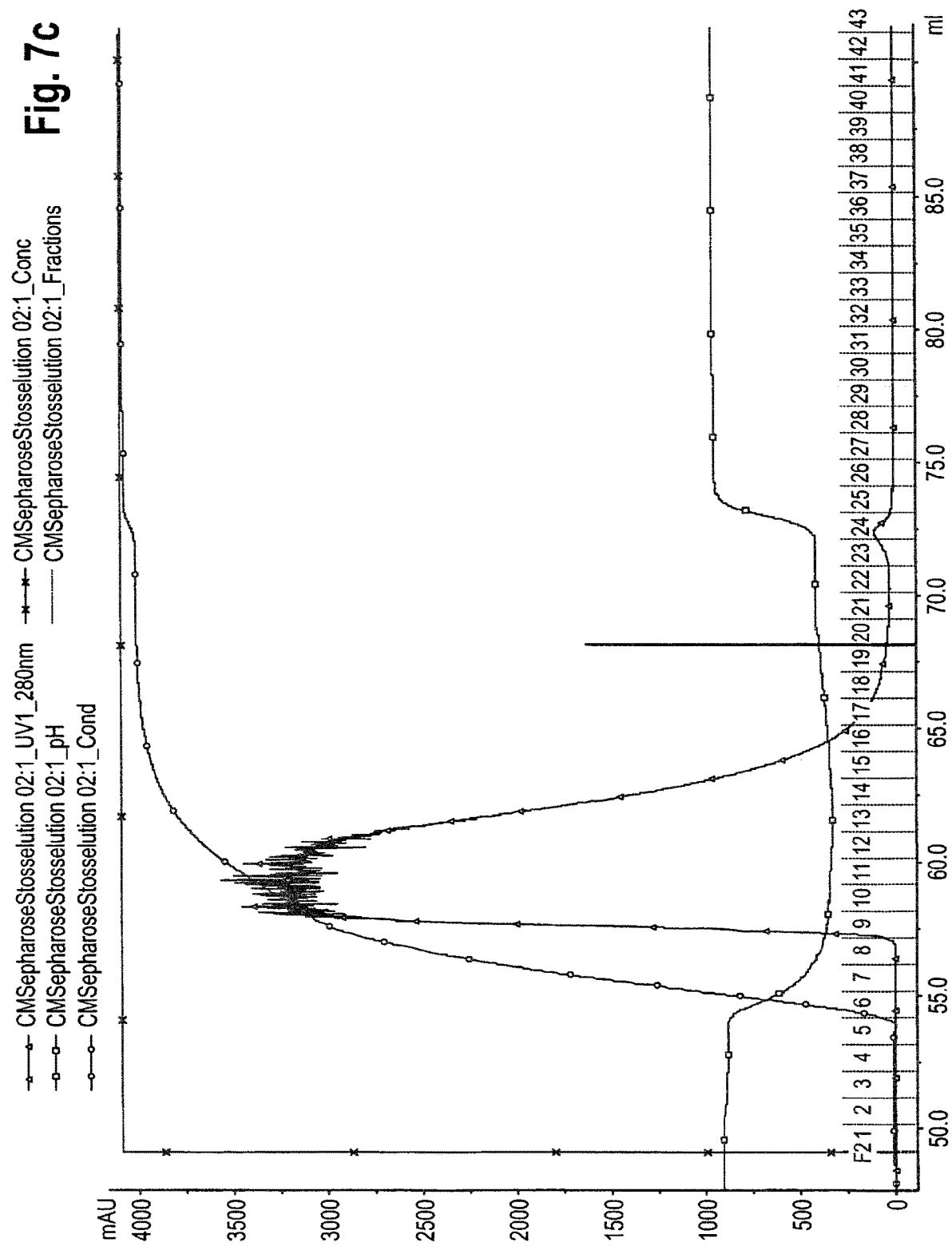
FIG. 7c Single step gradient elution of anti IL-1R antibody from weak cation exchange resin CM-Sepharose with 200 mM sodium chloride at pH 5.5.

The conditioned protein A eluate was applied to a chromatography column containing a weak cation exchange resin (CM-Sepharose). After the loading step at a flow rate of 160 cm/h the column was washed with equilibration buffer (10 column volumes). The bound immunoglobulins were eluted with a single step gradient elution method, whereby the pH value in the mobile phase was kept constant. The concentration of the buffer salt, sodium citrate, was kept constant and in three different runs 100 mM, 150 mM, and 200 mM sodium chloride respectively were admixed. After the increase of the salt concentration fifteen column volumes of the elution buffer were passed through the column to elute the bound immunoglobulin. The elution chromatograms are displayed in FIGS. 7a to c.

Good separations have been obtained using 150 mM sodium chloride and 200 mM sodium chloride as elution salt concentration.

Example 8

Comparative Example—Elution at Different pH Values

Chromatographic Conditions:
Resin: CM-Sepharose
Flow rate: 160 cm/h
Equilibration: 10 mM sodium citrate buffer, adjusted to pH 5.5
Loading: max. 20 g protein/L gel matrix
Wash: 10 mM sodium citrate buffer, adjusted to pH 5.5
Elution: 10 mM sodium citrate buffer with 150 mM sodium chloride, adjusted to pH 4.0, or 6.0

The conditioned protein A eluate was applied to a chromatography column containing a weak cation exchange resin (CM-Sepharose). After the loading step at a flow rate of 160 cm/h the column was washed with equilibration buffer (10 column volumes). The bound immunoglobulins were eluted with a single step gradient elution method, whereby the pH value in the mobile phase was kept constant at pH 4.0 or 6.0 respectively. The concentration of the buffer salt, sodium citrate, was kept constant, and 150 mM sodium chloride was admixed. After the increase of the salt concentration fifteen column volumes of the elution buffer were passed through the column to elute the bound immunoglobulin. The elution chromatograms are displayed in FIGS. 8*a* and *b*.

At pH 4.0 is the tendency to form aggregates of this immunoglobulin increased. But the CM-Sepharose is able to separate this higher amount of aggregates in two peaks.

Example 9

Chromatographic Separation of a Monoclonal Anti-HER-2 Antibody (WO 99/57134) with a Strong Cation Exchange Resin (SP-Sepharose).

The current invention is further exemplified in the following with Herceptin®, a monoclonal anti-HER-2 antibody.

The purification of Herceptin with a cation exchange chromatography on SP-Sepharose, a strong cation exchange resin, was carried out. Under standard conditions of the current invention, i.e. step elution with e.g. sodium chloride, a separation of monomeric and aggregated forms of the antibody is not effected (FIG. 10).

Chromatographic Conditions:
Resin: SP-Sepharose
Flow rate: 160 cm/h
Equilibration: 25 mM 2-morpholinoethanesulfonic acid, 50 mM sodium chloride, adjusted to pH 5.6
Loading: max. 20 g protein/L gel matrix
Wash: 25 mM 2-morpholinoethanesulfonic acid, 50 mM sodium chloride, adjusted to pH 5.6
Elution: 25 mM 2-morpholinoethanesulfonic acid, 95 mM sodium chloride, adjusted to pH 5.6

The monoclonal anti-HER-2 antibody (hereinafter referred to as Herceptin®) was purified in a first step with a protein A affinity chromatography. Elution from the protein A column is carried out under acidic conditions (10 mM sodium citrate buffer, pH value of 3.0±0.5). Before the filtration step the pH value of the fraction containing the antibody is adjusted with a concentrated tris-hydroxymethyl-aminomethane (TRIS) buffer to pH 5.6. The protein A eluate is a solution with a protein concentration between 5 mg/ml and 15 mg/ml and is buffered with sodium citrate.

The conditioned protein A eluate was applied to a chromatography column containing a strong cation exchange resin (SP-Sepharose). After the loading step at a flow rate of 160 cm/h the column was washed with equilibration buffer (10 column volumes). The bound immunoglobulins were eluted with a single step elution method, whereby the pH value was kept constant and the conductivity was varied by the (stepwise) increase of the sodium chloride concentration. The elution chromatogram is displayed in FIG. 10.

No separation of monomeric and aggregated forms of the antibody was achieved.

Example 10

Optimization of the Chromatographic Method—First Step: Linear Concentration Gradient.

To improve the separation of the two fractions the separation conditions have been optimized in accordance with the procedure as outlined with the anti IL-1R antibody.

In contrast to the anti IL-1R antibody optimization process a linear gradient of a (elution) salt, i.e. of sodium chloride, was used instead of a gradient of the buffer substance. The chromatogram of the linear sodium chloride gradient elution, which corresponds to the first step of the optimization procedure, is presented in FIG. 11. Analysis confirmed that the tail of the main peak is enriched with aggregated forms of the antibody.

Chromatographic Conditions:
Resin CM-Sepharose
Flow rate: 160 cm/h
Equilibration: 10 mM sodium citrate buffer, adjusted to pH 5.5
Loading: max. 20 g protein/L gel matrix
Wash: 10 mM sodium citrate buffer, adjusted to pH 5.5
Elution: linear gradient; from 10 mM sodium citrate buffer, adjusted to pH 5.5, to 10 mM sodium citrate buffer containing 400 mM sodium chloride, adjusted to pH 5.5

The conditioned protein A eluate as described in example 9 was applied to a chromatography column containing a weak cation exchange resin (CM-Sepharose). After the loading step at a flow rate of 160 cm/h the column was washed with equilibration buffer (10 column volumes). The bound immunoglobulins were eluted with a linear gradient elution method, whereby the pH value in the mobile phase and the concentration of the buffer salt was kept constant. The concentration of the elution salt, sodium chloride, was raised linearly from 0 mM to 400 mM over 40 column volumes. The elution chromatogram is displayed in FIG. 11.

The replacement of the strong cation exchange resin by a weak cation exchange resin caused the detachment of a second peak as shoulder of the first main peak. This observation is similar to the observation in case of the anti IL-1R antibody.

The immunoglobulins start to elute from the column at a sodium chloride concentration of 80 mM.

Example 11

Optimization of the Chromatographic Method—Second Step: Three Step Concentration Gradient Elution.

The starting concentration, at which the immunoglobulin starts to elute, as determined in example 10 and as derived from the chromatogram presented in FIG. 11, is 80 mM sodium chloride. For the calculation of the three concentration steps for the second optimization step the buffer concentration can be neglected as it is low and kept constant during the chromatography.

The starting concentration of the sodium chloride is 80 mM and sodium chloride has one cation different from hydrogen in its molecular formula. Accordingly the concentrations for the three step elution are calculated to be 80 mM, 100 mM (=80 mM multiplied with 1.25), and 120 mM (=80 mM multiplied with 1.50) sodium chloride respectively.

Chromatographic Conditions:
Resin: CM-Sepharose
Flow rate: 160 cm/h
Equilibration: 10 mM sodium citrate buffer, adjusted to pH 5.5
Loading: max. 20 g protein/L gel matrix
Wash: 10 mM sodium citrate buffer, adjusted to pH 5.5
Elution: step 1: 10 mM sodium citrate buffer with 80 mM sodium chloride, adjusted to pH 5.5
step 2: 10 mM sodium citrate buffer with 100 mM sodium chloride, adjusted to pH 5.5
step 3: 10 mM sodium citrate buffer with 120 mM sodium chloride, adjusted to pH 5.5

The conditioned protein A eluate as described in example 9 was applied to a chromatography column containing a weak cation exchange resin (CM-Sepharose). After the loading step at a flow rate of 160 cm/h the column was washed with equilibration buffer (10 column volumes). The bound immunoglobulins were eluted with a step gradient elution method, whereby the pH value in the mobile phase and the concentration of the buffer salt, sodium citrate, was kept constant. The concentration of the elution salt, sodium chloride, was raised from 0 mM as starting condition to 80 mM in the first step, to 100 mM in the second step, and to 120 mM in the final step. After each increase of the salt concentration ten column volumes of the elution buffer with the specified sodium chloride concentrations were passed through the column prior to the next concentration step. After the final sodium citrate concentration was reached the elution was continued for an additional 10 column volumes. The elution chromatogram is displayed in FIG. 12.

Figure 12:
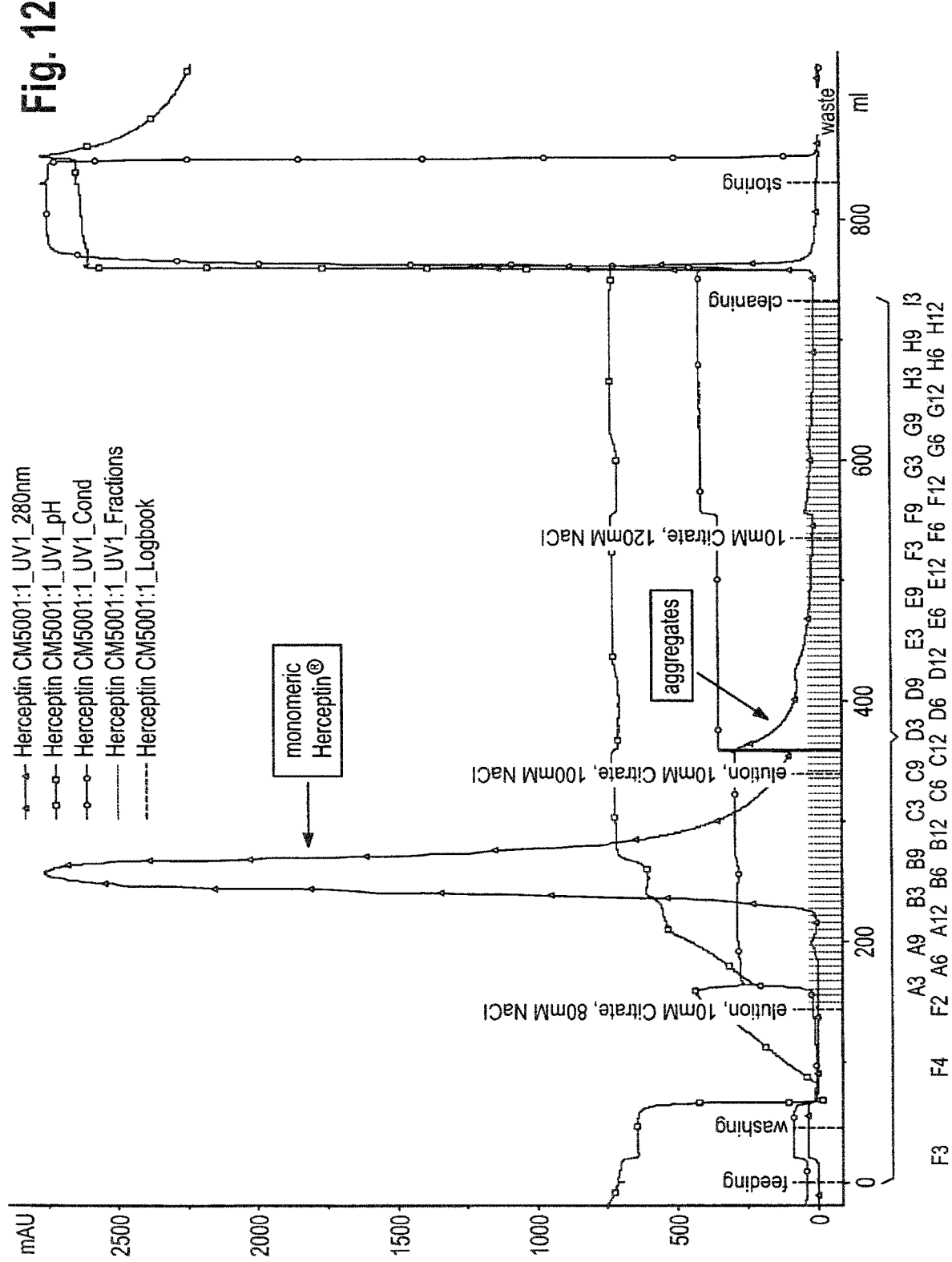
FIG. 12 Three step gradient elution of anti-HER-2 antibody from weak cation exchange resin CM-Sepharose with sodium chloride in sodium citrate buffer at pH 5.5; monomeric and aggregated forms of the antibody are separated and elute as one main peak comprising the monomeric form of the immunoglobulin at a sodium chloride concentration of 80 mM and as a second peak comprising monomeric and aggregated forms of the immunoglobulin as well as protein A at a sodium chloride concentration of 100 mM.

In the three step elution method the monomeric antibody is eluted at the step with a sodium chloride concentration of 80 mM. Size exclusion analysis confirmed that only monomeric antibody is eluted. After the sodium chloride concentration was increased to 100 mM in the second step, the aggregated forms eluted (FIG. 12).

Example 12

Optimization of the Chromatographic Method—Third Step: Single Step Elution with Sodium Chloride.

Chromatographic Conditions:
Resin: CM-Sepharose; SP-Sepharose
Flow rate: 160 cm/h
Equilibration: 10 mM sodium citrate, adjusted to pH 5.5
Loading: max. 20 g protein/L gel matrix
Wash: 10 mM sodium citrate, adjusted to pH 5.5
Elution: 10 mM sodium citrate with 80 mM sodium chloride, adjusted to pH 5.5

Figure 13:
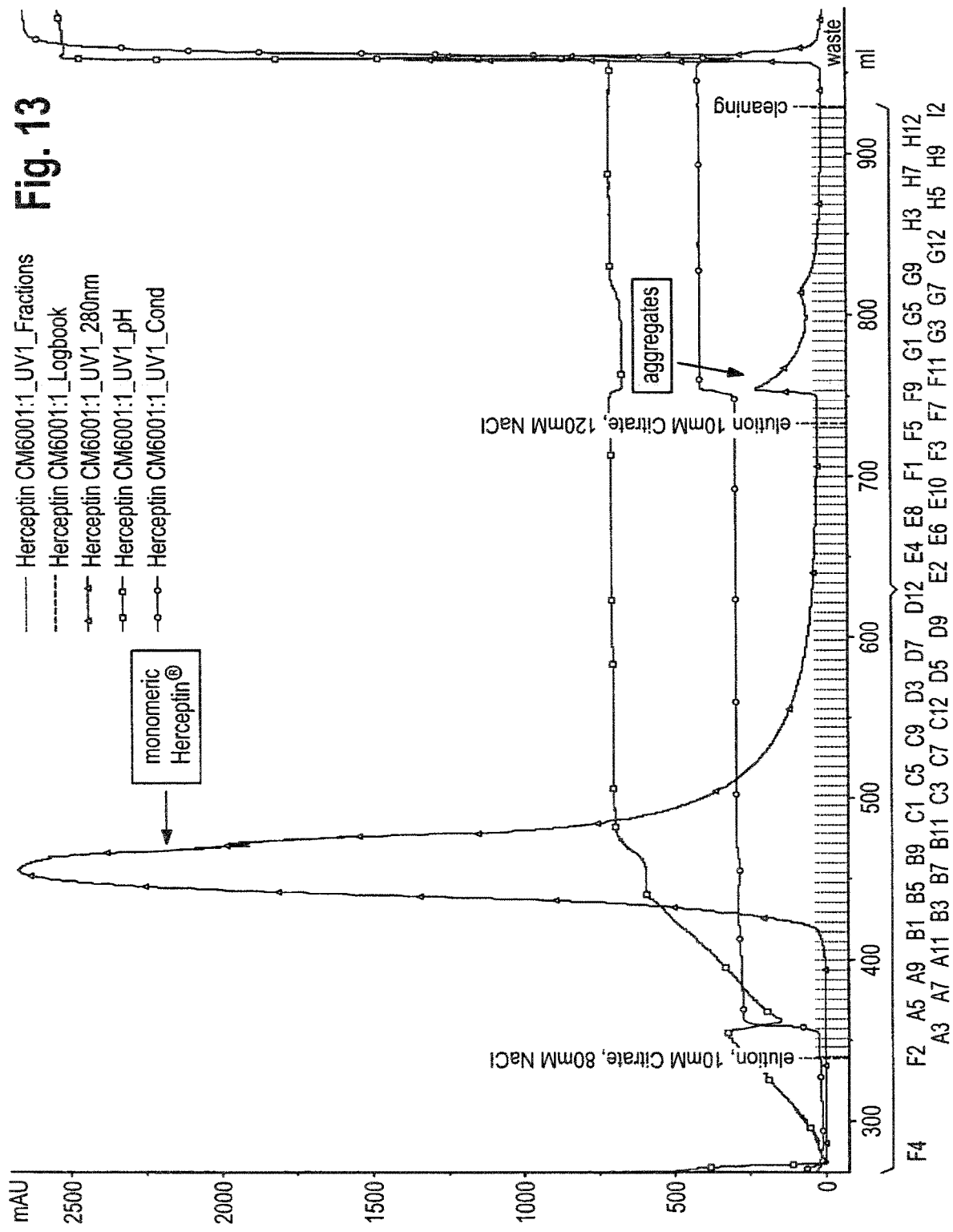
FIG. 13 Single step gradient elution of anti-HER-2 antibody from weak cation exchange resin CM-Sepharose with 80 mM sodium chloride at pH 5.5; the monomeric form is eluted free of aggregated forms; the aggregated forms elute after a second sodium chloride step to 120 mM as a second defined peak.

The conditioned protein A eluate as described in example 9 was applied to a chromatography column containing a weak cation exchange resin (CM-Sepharose). After the loading step at a flow rate of 160 cm/h the column was washed with equilibration buffer (10 column volumes). The bound immunoglobulins were eluted with a single step gradient elution method, whereby the pH value in the mobile phase and the concentration of the buffer salt was kept constant. The concentration of the buffer salt, sodium citrate, was kept constant and 80 mM sodium chloride was admixed. After the increase of the salt concentration fifteen column volumes of the elution buffer with sodium chloride were passed through the column to elute the bound anti-HER-2 antibody in monomeric form. To affirm the separation of monomeric and aggregated forms of the antibody a second step, which is not necessary for the preparation of monomeric antibodies, to a sodium chloride concentration of 120 mM was performed. After this second increase the aggregated forms of the antibody eluted from the column. The elution chromatogram is displayed in FIG. 13.

Figure 14:
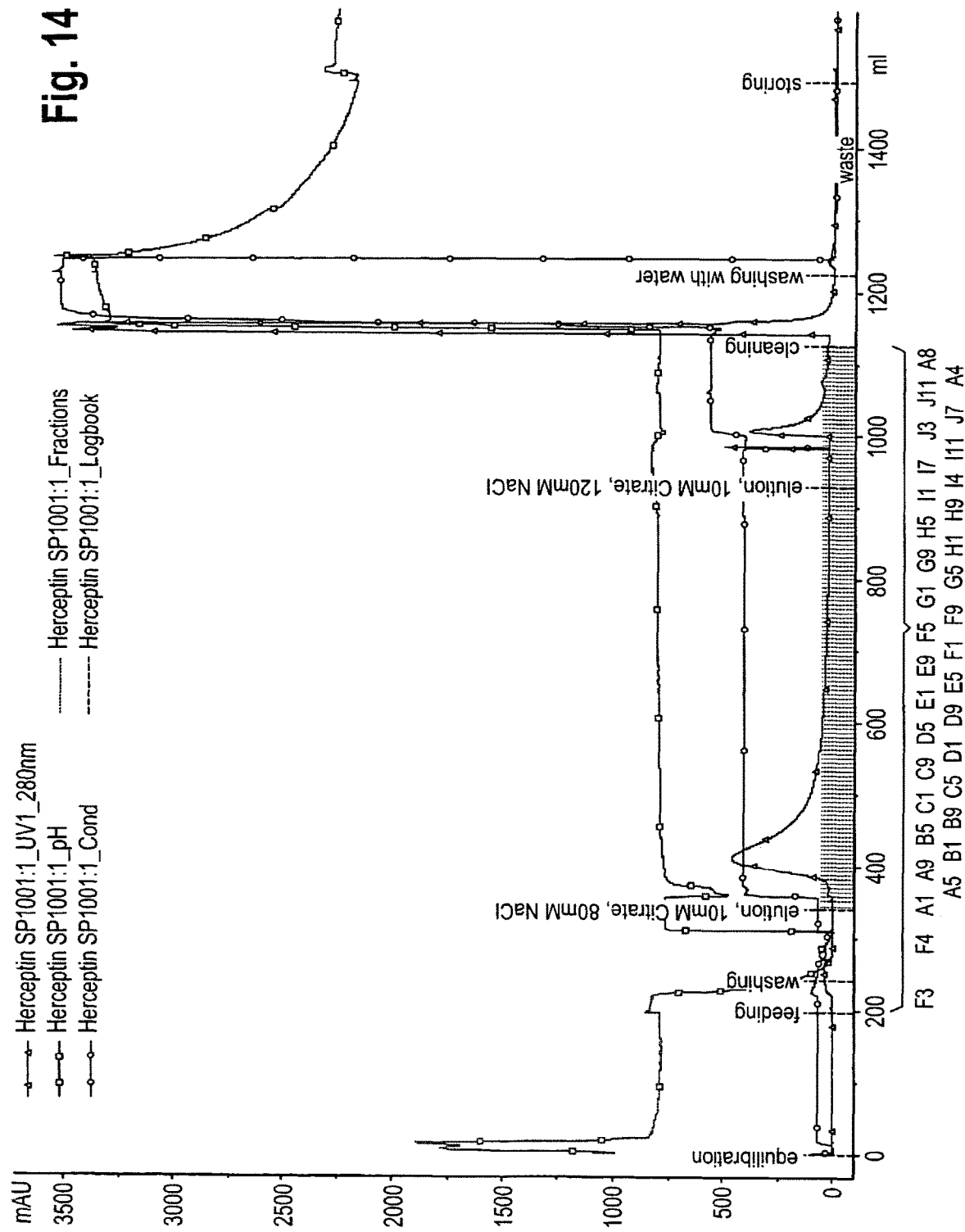
FIG. 14 Single step gradient elution of anti-HER-2 antibody from strong cation exchange resin SP-Sepharose with 80 mM sodium chloride at pH 5.5; two peaks are obtained: peak 1 contains only monomeric Herceptin®, peak 2, which is eluted after a second sodium chloride step to 120 mM, contains a high amount of monomeric Herceptin® and aggregates; the yield of Herceptin® in its monomeric form is less than 60%.

If the same method is performed with a strong cation-exchange resin a significant loss of monomeric antibody is observed (yield of approximately 60% only compared to 95% and more on a weak cation exchange column), although the separation of monomeric and aggregated form of the antibody can be seen (FIG. 14).

Applying the conditions suitable for the separation on a weak cation exchange material to a strong cation exchange resin, SP-Sepharose, is not beneficial. Albeit the two fractions can be separated the yield of the monomeric antibody is reduced to 60% or even less.

TABLE 2

Analysis of the eluates: comparison between SP-Sepharose and CM-Sepharose, results of two different separations are presented.

| analyte | conditioned protein A eluate | SP-Sepharose Peak 1 | SP-Sepharose Peak 2 | CM-Sepharose Peak 1 | | CM-Sepharose Peak 2 | |
|---|---|---|---|---|---|---|---|
| amount of protein A | 17 ng/mg | <3.9 ng/mg | 5.7 ng/mg | <3.9 ng/mg | <3.9 ng/mg | 32.2 ng/mg | 39.7 ng/mg |
| HCP | 3243 ng/mg | 49.0 ng/mg | 183.4 ng/mg | 107.5 ng/mg | 126.2 ng/mg | 1247 ng/mg | 988 ng/mg |
| DNA | 1615 pg/mg | 830 pg/mg | 2635 pg/mg | 319 pg/mg | 682 pg/mg | 10554 pg/mg | <9300 pg/mg |
| aggregates (SEC) | 0.97% | 0% | 32% | 0% | 0% | 15.2% | 23.0% |

The invention claimed is:

1. A method for purifying a monomeric monoclonal anti-HER2 antibody from aggregates thereof, wherein the method comprises:

a) purifying a monoclonal anti-HER2 antibody by protein A affinity chromatography;

b) providing a solution comprising the monoclonal anti-HER2 antibody of step a);

c) bringing the solution of step b) and a weak cation exchange material in contact under conditions whereby the monoclonal anti-HER2 antibody binds to the weak cation exchange material; and d) recovering the monomeric monoclonal anti-HER2 antibody from the weak cation exchange material in a single step by using a second solution comprising a buffer substance and a salt wherein the conductivity of the second solution is increased by changing one condition all at once from a starting value to a final value so as to obtain the monomeric monoclonal anti-HER2 antibody purified from aggregates thereof, wherein the buffer substance and salt are the same and the monoclonal anti-HER2 antibody has an isoelectric point (pI) of 6.0 or higher.

2. The method according to claim 1, wherein the buffer substance of step d) is selected from the group consisting of citric acid, a salt of citric acid, phosphoric acid, and a salt of phosphoric acid.

3. The method according to claim 1, wherein the method is a chromatographic or a batch method.

4. The method according to claim 1, wherein the salt of step d) is selected from the group consisting of sodium chloride, sodium sulphate, potassium chloride, potassium sulfate, salts of citric acid, salts of phosphoric acid, and mixtures thereof.

5. The method according to claim 2, wherein the method is a chromatographic or a batch method.

6. The method according to claim 1, wherein the pH is kept constant in the single step.

7. The method according to claim 2, wherein the pH is kept constant in the single step.

8. The method according to claim 3, wherein the pH is kept constant in the single step.

9. The method according to claim 1, wherein the salt in elution step d) is added at the same time as the buffer substance.

10. The method according to claim 1, wherein the weak cation exchange material is a carboxy-methyl weak cation exchange material.

11. The method according to claim 1, wherein the monoclonal anti-HER2 antibody is a member of the immunoglobulin class G.

12. The method according to claim 1, wherein the second solution in the recovery step d) has a pH value of from pH 3.0 to pH 7.0.

13. The method according to claim 2, wherein the weak cation exchange material is a carboxy-methyl weak cation exchange material.

* * * * *